United States Patent
Saadat et al.

(10) Patent No.: US 8,087,413 B2
(45) Date of Patent: Jan. 3, 2012

(54) ATTENUATION OF ENVIRONMENTAL PARAMETERS ON A GASTRIC LUMEN

(75) Inventors: Vahid Saadat, Saratoga, CA (US);
Ruey-Feng Peh, Singapore (SG);
Richard C. Ewers, Fullerton, CA (US);
Eugene G. Chen, Carlsbad, CA (US)

(73) Assignee: USGI Medical Inc., San Clemente, CA (US)

( * ) Notice: Subject to any disclaimer, the term of this patent is extended or adjusted under 35 U.S.C. 154(b) by 1642 days.

(21) Appl. No.: 11/035,702

(22) Filed: Jan. 14, 2005

(65) Prior Publication Data
US 2006/0157067 A1    Jul. 20, 2006

(51) Int. Cl.
*A61B 19/00* (2006.01)
*A61B 17/08* (2006.01)
*A61B 17/04* (2006.01)
*A61F 2/04* (2006.01)
*A61L 17/00* (2006.01)

(52) U.S. Cl. ............ 128/898; 623/23.65; 606/151; 606/153; 606/228; 606/232

(58) Field of Classification Search .......... 606/151–156, 606/232; 623/23.65; 128/898
See application file for complete search history.

(56) References Cited

U.S. PATENT DOCUMENTS

| | | | |
|---|---|---|---|
| 6,558,400 B2 * | 5/2003 | Deem et al. ............... | 606/151 |
| 6,821,285 B2 | 11/2004 | Laufer et al. | |
| 6,835,199 B2 | 12/2004 | McGuckin, Jr. et al. | |
| 6,981,978 B2 * | 1/2006 | Gannoe ..................... | 606/153 |
| 7,131,978 B2 * | 11/2006 | Sancoff et al. ............ | 606/139 |
| 7,153,314 B2 * | 12/2006 | Laufer et al. .............. | 606/153 |
| 7,431,725 B2 * | 10/2008 | Stack et al. ............... | 606/151 |
| 2004/0122474 A1 | 6/2004 | Gellman et al. | |
| 2004/0193117 A1 | 9/2004 | Laufer et al. | |
| 2004/0193184 A1 | 9/2004 | Laufer et al. | |
| 2004/0193193 A1 | 9/2004 | Laufer et al. | |
| 2004/0193194 A1 | 9/2004 | Laufer et al. | |

(Continued)

FOREIGN PATENT DOCUMENTS

WO    WO 02/060328 A1    8/2002

(Continued)

OTHER PUBLICATIONS

Chuttani et al., "A Novel Endoscopic Full-thickness Plicator for Treatment of GERD: An Animal Model Study," *Gastrointestinal Endoscopy*, vol. 26, No. 1,( 2002), pp. 116-122.
Mason, "Development of Future of Gastroplasties for Morbid Obesity," *Arch Surg*, vol. 138 (Apr. 2003), pp. 362-366.

*Primary Examiner* — Thomas J Sweet
*Assistant Examiner* — Andrew Iwamaye
(74) *Attorney, Agent, or Firm* — Levine Bagade Han LLP

(57) ABSTRACT

The attenuation or isolation of environmental parameters on a gastric lumen is described herein. Once tissue plications are formed into a gastric lumen or sleeve within a stomach, the newly formed lumen is subjected to a multitude of fluctuating stresses or pressure from food or fluids passing therethrough, from naturally-occurring contractions, and/or from changes in pH levels from caustic stomach acids and hormones. The tissue interface between these plications can be isolated from such environmental fluctuations, or the fluctuations can be attenuated, by a number of methods. One example is to place a gastric stent or sleeve within the newly formed lumen. Another example is to utilize multiple rows of anchors, clips, or sutures along the interface. Alternatively, bio-adhesives can be dispensed to buttress the tissue interface. In another variation, the tissue can be approximated in different configurations which effectively reduce or isolate the adhered tissue region.

25 Claims, 21 Drawing Sheets

U.S. PATENT DOCUMENTS

| | | |
|---|---|---|
| 2004/0194790 A1 | 10/2004 | Laufer et al. |
| 2004/0210243 A1 | 10/2004 | Gannoe et al. |
| 2004/0215216 A1* | 10/2004 | Gannoe et al. ............... 606/151 |
| 2004/0243152 A1 | 12/2004 | Taylor et al. |
| 2004/0249362 A1 | 12/2004 | Levine et al. |
| 2005/0033320 A1 | 2/2005 | McGuckin, Jr. et al. |
| 2005/0033328 A1* | 2/2005 | Laufer et al. ............... 606/153 |
| 2005/0043758 A1 | 2/2005 | Golden et al. |
| 2005/0049617 A1 | 3/2005 | Chatlynne et al. |
| 2005/0250980 A1* | 11/2005 | Swanstrom et al. ............ 600/37 |
| 2006/0157067 A1* | 7/2006 | Saadat et al. ............... 128/898 |
| 2006/0249165 A1* | 11/2006 | Silverman et al. ............ 128/898 |
| 2006/0282087 A1* | 12/2006 | Binmoeller ............... 606/139 |
| 2007/0135825 A1* | 6/2007 | Binmoeller ............... 606/153 |

FOREIGN PATENT DOCUMENTS

| | | |
|---|---|---|
| WO | WO 03/092509 A1 | 11/2003 |
| WO | WO 03/094785 A1 | 11/2003 |
| WO | WO 03/105732 A1 | 12/2003 |
| WO | WO 2004/004542 A2 | 1/2004 |
| WO | WO 2004/019788 A2 | 3/2004 |
| WO | WO 2004/021894 A1 | 3/2004 |
| WO | WO 2004/056273 A1 | 7/2004 |
| WO | WO 2004/084808 A2 | 10/2004 |
| WO | WO 2004/103189 A1 | 12/2004 |
| WO | WO 2005/037152 A1 | 4/2005 |

* cited by examiner

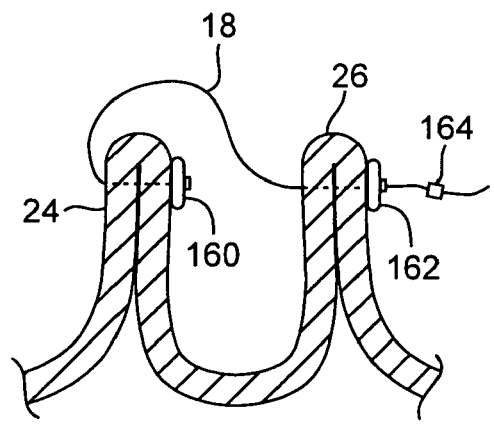
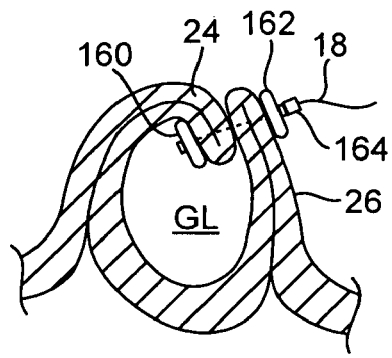
FIG. 20A    FIG. 20B
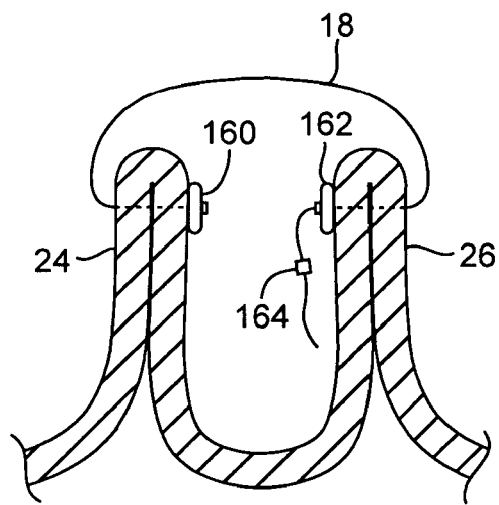
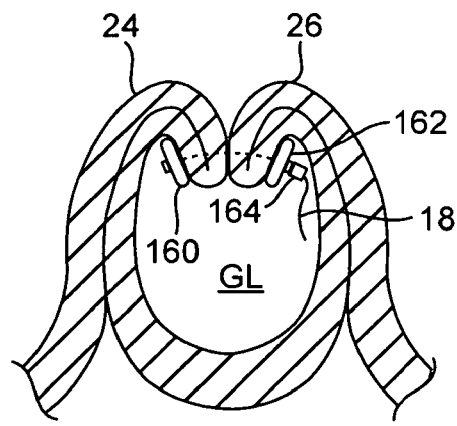
FIG. 21A    FIG. 21B

ATTENUATION OF ENVIRONMENTAL PARAMETERS ON A GASTRIC LUMEN

BACKGROUND OF THE INVENTION

Field of the Invention

The present invention relates to apparatus and methods for isolating a region of tissue. More particularly, the present invention relates to apparatus and methods for isolating a tissue interface formed within a gastrointestinal lumen from environmental factors.

When joining regions of tissue to one another, particularly tissue located within or along the gastrointestinal tract, it is generally desirable to securely join the tissue regions to one another. Such regions of joined tissue are typically secured to one another through various methods, e.g., suturing with surgical thread or stapling with a number of surgical staples. However, the gastrointestinal region, particularly within a stomach, presents an extremely dynamic environment with constant tissue movement caused by the natural motion of the gastrointestinal tissue in digesting and/or absorbing food.

Furthermore, adhering tissue regions to one another within the gastrointestinal region also present a challenge because of the presence of caustic biological fluids, the presence of food particles, and the nature of moist pliable tissue, among other factors. Such factors make the joining of tissue regions and the maintenance of the joined tissue difficult. Moreover, both suturing and stapling are susceptible to failure if the tissue adjacent to the suture or staple tears and allows for the suture or staples to work free from the joined tissue.

The maintenance of the joined tissue regions is made even more challenging when utilizing minimally invasive endoscopic tissue approximation and/or securement techniques. One application involving the approximation and securement of tissue regions within the gastrointestinal lumen is gastroplasty for, e.g., the treatment of obesity, where a gastric pouch in communication with the esophagus may be formed within the stomach to result in a volume which is less than the volume of an intact stomach.

In the instance where a gastric pouch is formed, the approximated regions of the tissue which are secured to one another via, e.g., tissue anchors, staples, suture, clips, adhesives, etc., may see an increase in pressure exerted by the tissue caused possibly by the ingestion of food or liquids or by excessive physical activity by the patient. This increased amount of pressure or stress may in turn stretch the approximated tissue to the point where the joined tissue, or a portion of it, is undone either by torn tissue regions or by a break in the securement mechanism.

A typical variable in the success of keeping such tissue joined together is the quality of the tissue anchor or securement. However, other measures which may decrease the overall pressure or stress imparted upon the approximated tissue are desirable.

BRIEF SUMMARY OF THE INVENTION

A tissue plication tool having a distal tip may be advanced (transorally, transgastrically, etc.) into a stomach to create uniform plications of predetermined size. In order to create the plication within a body lumen of a patient, various methods and devices may be implemented. The anchoring and securement devices may be delivered and positioned via an endoscopic apparatus that engages a tissue wall of the gastrointestinal lumen, creates one or more tissue folds, and disposes one or more of the anchors through the tissue fold(s).

The tissue anchor(s) may be disposed through the muscularis and/or serosa layers of the gastrointestinal lumen. Examples of apparatus which are particularly suited to deliver the anchoring and securement devices and examples of creating and forming tissue plications may be seen in further detail in co-pending U.S. patent application Ser. Nos. 10/840,950 filed May 7, 2004 and 10/954,666 filed Sep. 29, 2004, which are incorporated herein by reference in their entirety.

Once the tissue plications are formed into a gastric lumen or sleeve within the main stomach, the newly formed gastric lumen may be subjected to a multitude of fluctuating stresses or pressure from food or fluids passing therethrough. Fluctuating pressure may also be imparted from the main lumen by naturally-occurring stomach contractions or from movement of the stomach relative to the gastric lumen. The tissue interface of the approximated folds forming the gastric lumen may also be exposed to other environmental fluctuations such as changes in pH levels from caustic stomach acids and hormones.

Although the tissue interface need not necessarily be formed as a food- or fluid-tight seal, maintaining prolonged and uninterrupted contact along the length of the interface may be desirable under some circumstances to promote healing or in-growth between the contacting tissue between the folds. Accordingly, isolating the region of tissue interface (or at least attenuating the resulting fluctuations imparted on the tissue interface) from fluctuations in pressure, stress, chemical changes, or other parameters within the environment of the stomach may be achieved through various methods and apparatus.

The tissue interface may be isolated or attenuated in one variation by forming a gastric lumen and placing a sleeve or stent within the gastric lumen. The sleeve or stent may be positioned within the gastric lumen either intra-operatively or post-operatively of forming gastric lumen. Once the sleeve or stent is placed, ingested food or fluids may then pass through the sleeve or stent which acts as a barrier to prevent the ingested products from directly contacting the tissue interface. The sleeve or stent may be left in the gastric lumen temporarily until the tissue interface has healed or adhered or it may be left within gastric lumen permanently, depending upon the desired effects.

In another variation, a second row of clips or sutures may be deployed to function as an oversew (intermittent or running) to help secure the tissue folds to one another and to facilitate the tissue adhesion along the joined length of approximated tissue. The region of approximated tissue below the oversew along the tissue interface where the tissue folds are fastened by the tissue anchors may act as a barrier to fluctuating pressures imparted from the gastric lumen or other environmental fluctuations. The second row of clips or sutures may be positioned in an adjacent linear pattern where the rows are directly adjacent to one another. Alternatively, the second row may be placed in a staggered pattern relative to the other row of anchors.

Aside from utilizing multiple rows of tissue anchors to attenuate or isolate environmental fluctuations from the approximated tissue folds, another method may include the placement of biocompatible adhesives along or around the adhesion regions between the tissue folds. Such a bio-adhesive may be applied above the secured tissue folds, below the tissue anchors within gastric lumen, or between to buttress the tissue adhesion by tissue anchors. Alternatively, the bio-adhesive may optionally be dispensed along the apposed tissue folds within gaps along the tissue contact region in the areas in-between the tissue anchors.

Aside from the use of bio-adhesives, the tissue regions within the stomach may themselves be arranged and plicated in such a way as to facilitate the alleviation of pressures and other environmental fluctuations from the adhered and secured regions of tissue forming gastric lumen. For instance, a first anchor securement assembly may secure two tissue folds extending into the gastric lumen. These folds extending partially into the separated main lumen may also be used to form an additional adjacent plication using a second anchor securement assembly. Thus, the two adjacent sets of tissue folds utilize common folds of tissue in a back-to-back manner. This manner of adhering and securing the tissue folds may effectively isolate the region of tissue between the respective tissue securement assemblies from environmental fluctuations.

Alternatively, the second anchor securement assembly may be used to approximate and secure regions of tissue from within the main lumen to further divide the main lumen into a first main lumen and second main lumen. The second set of folds may be secured such that they are immediately adjacent to or directly lie upon the first set of folds. Such a configuration may also effectively isolate the approximated tissue folds of gastric lumen from the fluctuations experienced by the remaining stomach.

Another variation utilize connecting anchors with lengths of suture that are deployed such that they loops over the tissue folds and come back through the folds to invert at least one tissue fold relative to the other. Yet another configuration may utilize lengths of suture that are placed in a crossing configuration relative to one another. The tissue anchors may be paired to form discrete sets of crossed sutures. Alternatively, the tissue anchors may be paired to form staggered and/or interconnected crossed sutures.

Aside from inverting a tissue fold, the tissue anchors may be deployed such that they are positioned within the gastric lumen. Thus, the suture interconnecting the anchors may be looped over the tissue interface and drawn down to simulate a suture oversew. Such an arrangement may be utilized to create intermittent or running sutures over the length (or a partial length) of the gastric lumen.

In yet another variation, one or more tissue anchors may be deployed exteriorly of the gastric lumen to be formed. These exterior tissue anchors may be drawn together to loosely approximate the tissue folds and a number of additional tissue anchors may then be deployed interiorly of gastric lumen such that the suture forms a suture oversew.

BRIEF DESCRIPTION OF THE DRAWINGS

FIGS. 20A and 20B illustrate another variation for approximating overlapped tissue folds having an adhesion region isolated from fluctuations.

FIGS. 21A and 21B illustrate yet another variation for approximating inverted tissue regions.

DETAILED DESCRIPTION OF THE INVENTION

In creating tissue plications, a tissue placation tool having a distal tip may be advanced (transorally, transgastrically, etc.) into the stomach. The tissue may be engaged or grasped and the engaged tissue may be moved to a proximal position relative to the tip of the device, thereby providing a substantially uniform placation of predetermined size.

Generally, in creating a placation through which a tissue anchor may be disposed within or through, a distal tip of a tissue plication apparatus may engage or grasp the tissue and move the engaged tissue to a proximal position relative to the tip of the device, thereby providing a substantially uniform placation of predetermined size.

In operation, a tissue grabbing assembly engages or grasps the tissue wall in its normal state (i.e., non-folded and substantially flat) and is then moved proximally to form the tissue fold. The tissue anchor assembly then may be extended across the tissue fold. Examples of apparatus which are particularly suited to deliver the anchoring and securement devices and examples of creating and forming tissue plications may be seen in further detail in co-pending U.S. patent application Ser. Nos. 10/840,950 filed May 7, 2004 and 10/954,666 filed Sep. 29, 2004, which are incorporated herein by reference in their entirety.

Figure 1:
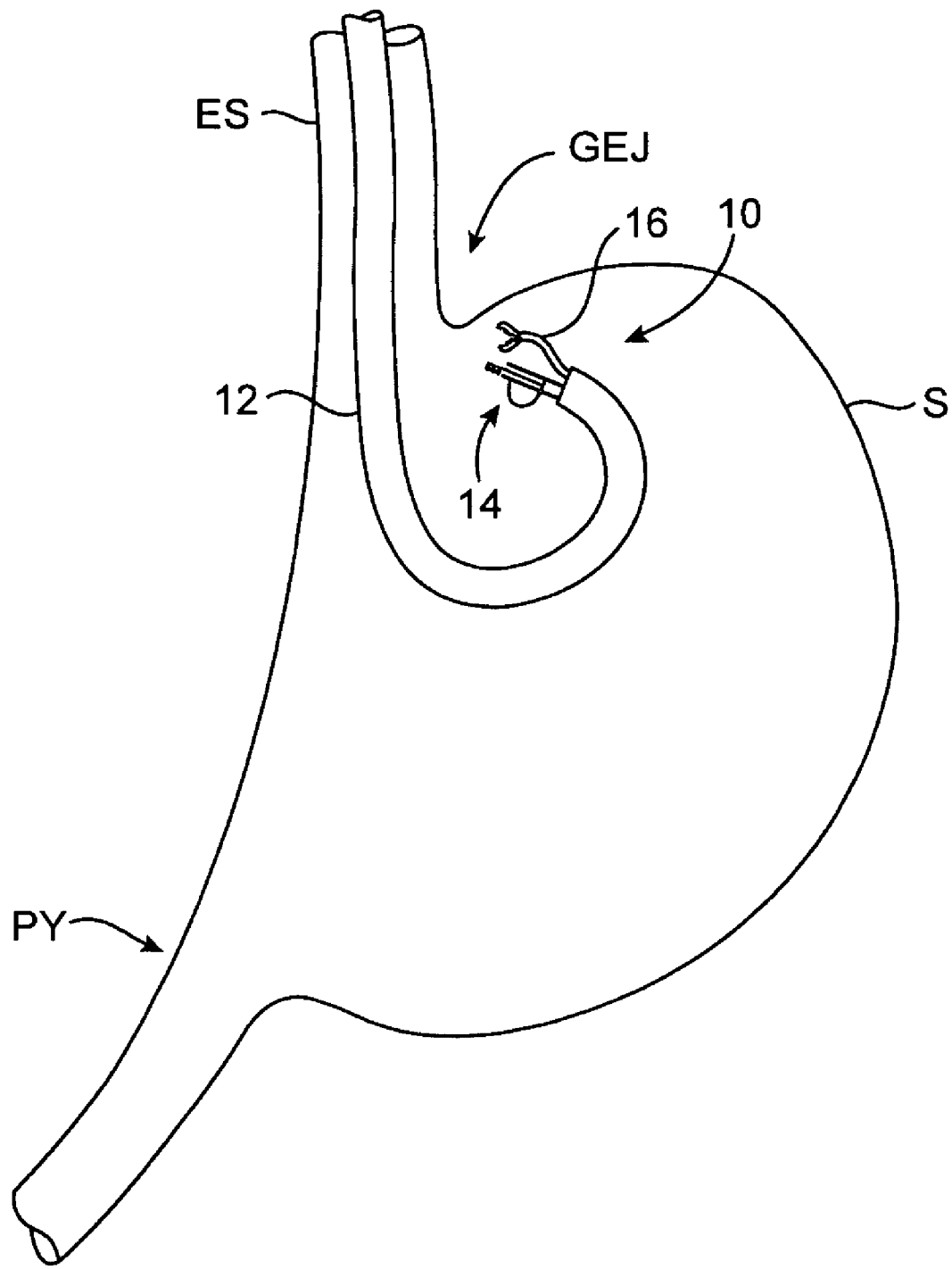
FIG. 1 illustrates one example of a tissue approximation and securement device which may be advanced per-orally via an endoscopic device for performing a procedure upon the tissue.

One method of forming a plurality of tissue plications is shown in FIG. 1, which illustrates one example of a tissue manipulation assembly 10 which may be advanced per-orally through an esophagus ES, past gastroesophageal junction GEJ, and into a stomach S via an endoscopic device 12. As shown, a tissue approximation and securement device 14, as shown in greater detail in Ser. Nos. 10/840,950 and 10/954,666 incorporated above by reference, may be advanced through endoscopic device 12 and into stomach S to perform a tissue manipulation procedure. A tissue manipulation tool 16, e.g., graspers, forceps, etc., may optionally be advanced within a lumen defined through endoscopic device 12.

Figure 2:
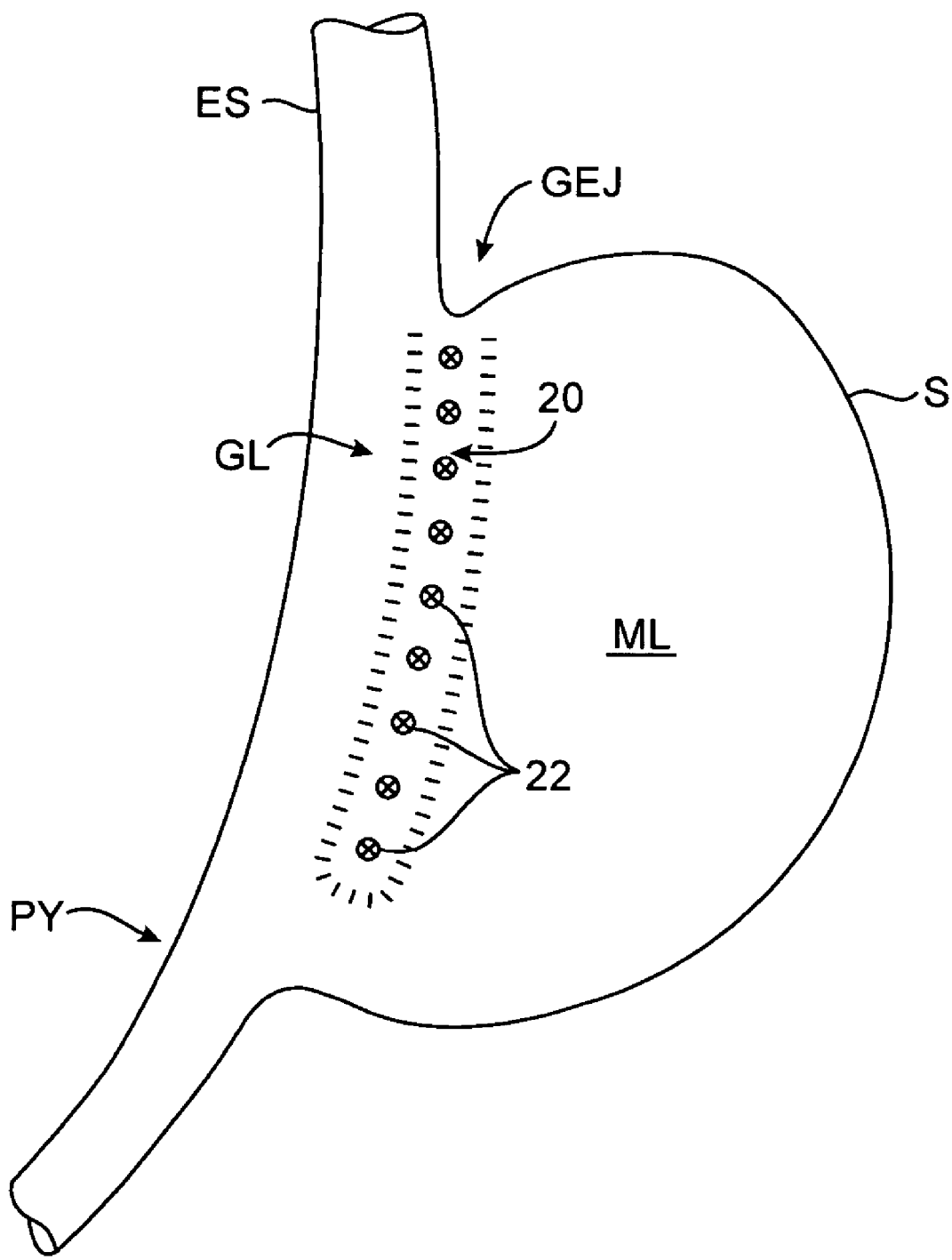
FIG. 2 shows one example of a procedure which may be performed utilizing the device of FIG. 1 to form a gastric lumen within a stomach.

FIG. 2 shows one example of a resulting gastric lumen GL which may be formed within stomach S utilizing the tools and methods described above. Tissue ridge 20 may be formed to extend from GEJ to pylorus PY by deploying a plurality of expandable tissue anchors 22 to secure tissue plications. The gastric lumen GL may then form a gastric pouch separate from the main lumen ML of stomach S to act as a restriction to the passage of food or fluids therethrough.

Figure 3A:
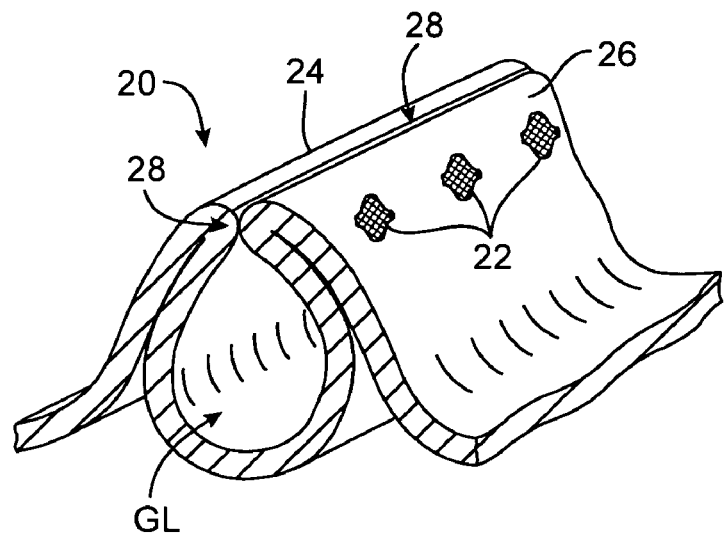
FIG. 3A shows a partial perspective view of the resulting gastric lumen of FIG. 2.
Figure 3B:
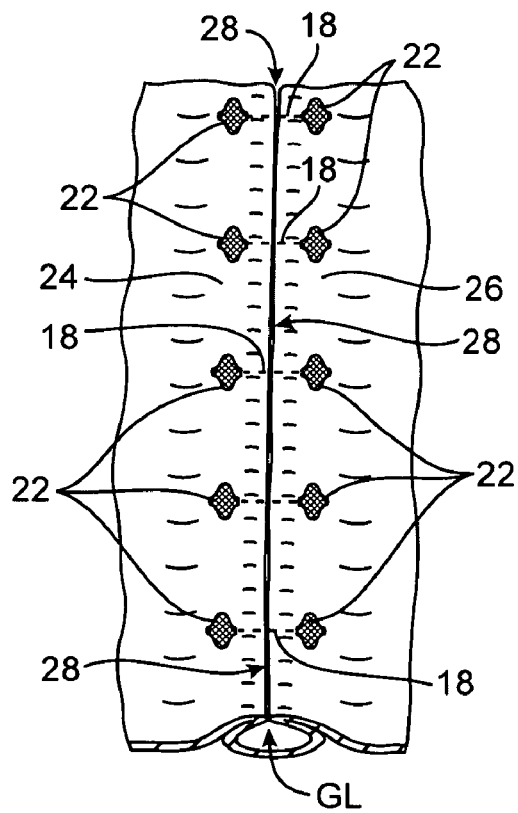
FIG. 3B shows a top view of the joined tissue regions forming the gastric lumen of FIG. 3A.

FIGS. 3A and 3B show partial perspective and top views, respectively, of the resulting gastric lumen GL of FIG. 2. Anterior tissue fold 24 and posterior tissue fold 26 may be seen to contact one another along tissue contact interface or region 28 while forming gastric lumen GL between the respective folds 24, 26. The integrity of gastric lumen GL may be maintained by a plurality of expandable tissue anchors 22 which may be deployed on either side of interface 28. Each of the tissue anchors 22 may be paired such that each anchor may be connected via a wire or suture 18 to a respective tissue anchor on an opposite side of interface 28, as shown in FIG. 3B. Various expandable tissue anchors and methods for tissue plication are described in further detail in U.S. patent application Ser. Nos. 10/840,950 filed May 7, 2004 and 10/869,472 filed Jun. 15, 2004, each of which are incorporated herein by reference in its entirety.

Because the gastric lumen GL is formed to communicate directly with esophagus ES and extends towards pylorus PY, food and fluids ingested by a patient initially enters the upper proximal portion of gastric lumen GL and passes through the lumen GL and directly into pylorus PY. Once formed, gastric lumen GL may be subjected to a multitude of fluctuating stresses or pressure from food or fluids passing therethrough. Fluctuating pressure may also be imparted from the main lumen ML by naturally-occurring stomach contractions or from movement of the stomach S relative to the gastric lumen GL. Tissue interface 28 and gastric lumen GL may also be exposed to other environmental fluctuations such as changes in pH levels from caustic stomach acids and hormones.

Although tissue interface 28 need not necessarily be formed as a food- or fluid-tight seal, maintaining prolonged and uninterrupted contact along the length of interface 28 may be desirable under some circumstances to promote healing or in-growth between the contacting tissue between the folds 24, 26. Accordingly, isolating the region of tissue interface 28 (or at least attenuating the resulting fluctuations imparted on tissue interface 28) from fluctuations in pressure, stress, chemical changes, or other parameters within the environment of the stomach may be achieved through various methods and apparatus.

Tissue interface 28 may be isolated or attenuated in one variation by forming a gastric lumen GL and placing a sleeve or stent within gastric lumen GL. The sleeve or stent may be positioned within gastric lumen GL either intra-operatively or post-operatively of forming gastric lumen GL. Once the sleeve or stent is placed within gastric lumen GL, ingested food or fluids may then pass through the sleeve or stent which acts as a barrier to prevent the ingested products from directly contacting tissue interface 28. The sleeve or stent may be left in gastric lumen GL temporarily until tissue interface 28 has healed or adhered or it may be left within gastric lumen GL permanently, depending upon the desired effects.

The sleeve or stent may generally span the length of gastric lumen GL or just a portion of it and it may be fixedly attached to portions of the tissue within gastric lumen GL. Moreover, the sleeve or stent may be fabricated from a variety of materials and configured in a variety of embodiments. For instance, the sleeve or stent may be made as a wire-frame tubular structure with biocompatible polymeric materials or superelastic alloys such as Nitinol. The wire-frame structure may be optionally coated or covered with a lubricious material. Alternatively, the sleeve or stent may be fabricated from as a uniform sleeve of material rather than as a wire-frame. In either case, the sleeve or stent may be configured as a radially expandable structure capable of complying with movements of the stomach or peristaltic movement within gastric lumen GL. Alternatively, the sleeve or stent may be configured as a semi-rigid structure which may or may not be radially expandable.

Figure 4A:
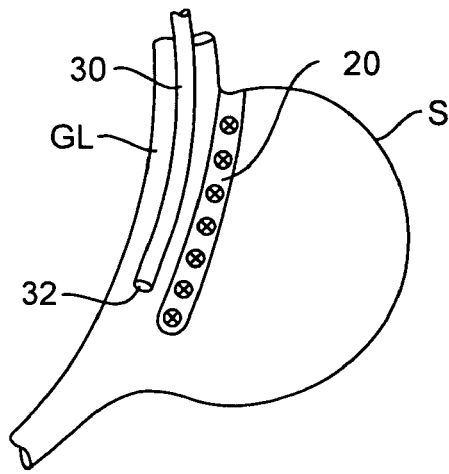
FIGS. 4A to 4C show one example for deploying a sleeve or stent within the gastric lumen from an endoscopic device or sheath for alleviating pressure exerted upon the joined ridges of tissue.
Figure 4B:
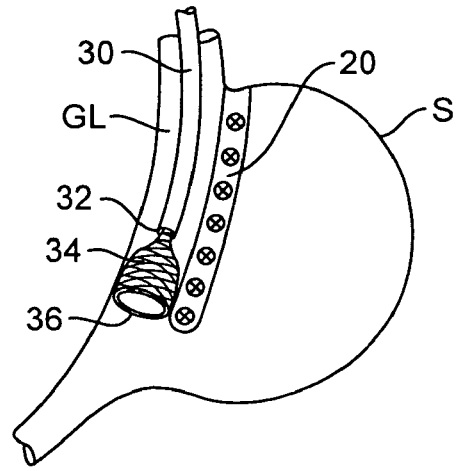
Figure 4C:
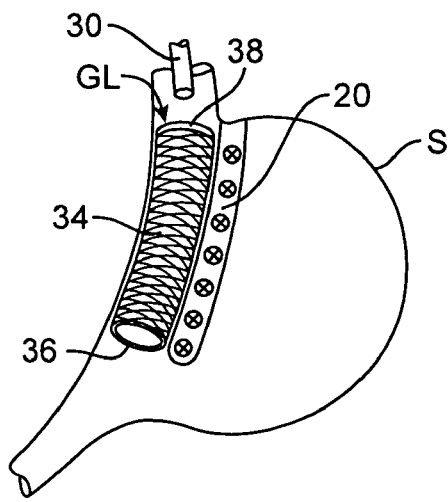

One example for the deployment of a gastric stent or sleeve within gastric lumen GL may be seen in FIGS. 4A to 4C, which illustrates a side view of a sleeve or stent being deployed via an endoscopic device. In FIG. 4A, an endoscopic delivery device, such as a conventional endoscope or overtube 30, is advanced through gastric lumen GL until the distal end of endoscope 30 is advanced near or at the terminal end of tissue ridge 20. An expandable sleeve or stent 34, having a distal anchoring region 36 in this example, may then be urged through the working lumen and out of opening 32 defined at the distal end of endoscope 30. As the sleeve or stent 34 is deployed, endoscope 30 may be pulled proximally through gastric lumen GL, as shown in FIG. 4B, until sleeve or stent 34 has been fully deployed from endoscope 30, as shown in FIG. 4C. The proximal end 38 of sleeve or stent 34 may also be anchored to the surrounding tissue adjacent to, proximally of, or distally of GEJ.

Figure 5:
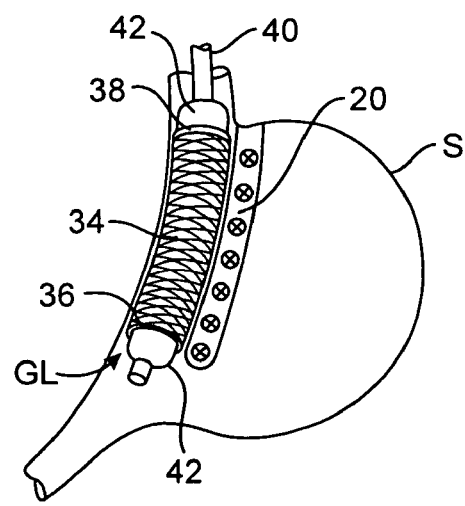
FIG. 5 shows another example for deploying a sleeve or stent via an expandable balloon.

Another example for deploying a gastric sleeve or stent may be seen in FIG. 5, which shows endoscopic delivery device 40, e.g., an endoscope, having an expandable balloon or scaffold 42 disposed over a distal portion of endoscopic device 40. Gastric sleeve or stent 34 may be placed over an unexpanded balloon or scaffold 42 in a low-profile delivery configuration when delivered through the esophagus and into gastric lumen GL. When desirably positioned, balloon or scaffold 42 may be actuated to expand and to thereby expand gastric sleeve or stent 34 into contact against the tissue walls of gastric lumen GL. Balloon or scaffold 42 may then be deflated or collapsed to allow for the proximal retraction of endoscopic device 40 proximally back through the esophagus.

Figure 6:
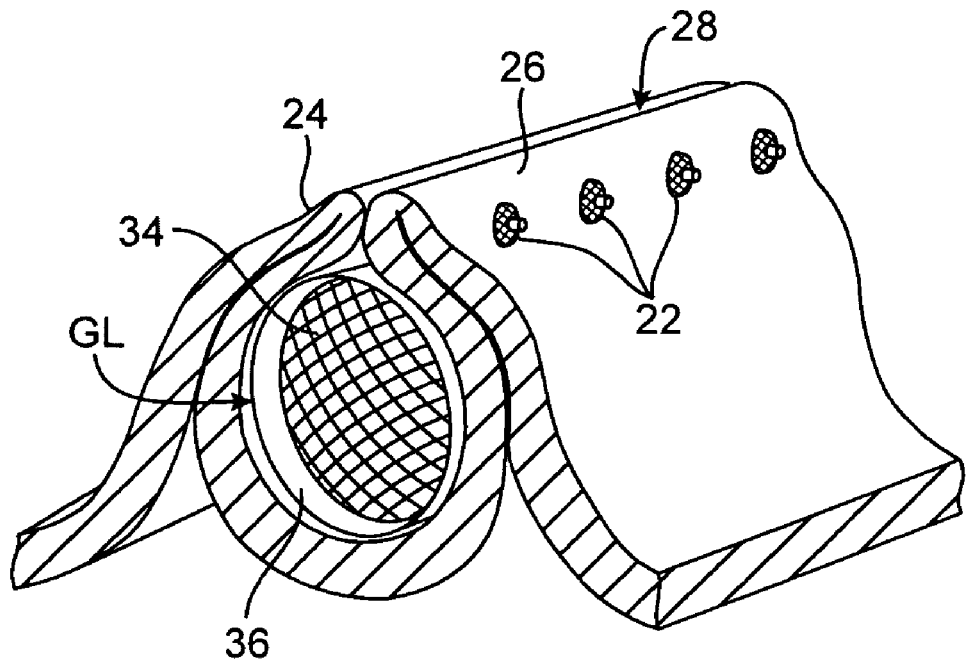
FIG. 6 shows a partial perspective view of a deployed and expanded sleeve or stent within the gastric lumen.

FIG. 6 shows a partial cross-sectional perspective view of the approximated tissue folds 24, 26 and the respective placement of gastric sleeve or stent 34 within gastric lumen GL. Sleeve or stent 34 may be anchored via anchoring region 36 utilizing any number of conventional methods for securement to the tissue, e.g., hooks, barbs, adhesives, etc.

The sleeve or stent may be left within gastric lumen GL for a limited period of time, e.g., a length of time sufficient to allow for the tissue ridge 20 to heal uninterrupted by the passage of ingested food or liquids. The sleeve or stent may then be removed from the gastric lumen GL using any number of conventional removal techniques. Alternatively, as mentioned above, the sleeve or stent may be left in place within the gastric lumen GL indefinitely.

Any number of available sleeves or stents which are suitable for deployment within gastric lumen GL may be utilized. For instance, the Ultraflex™ Esophageal NG Stent manufactured by Boston Scientific (Natick, Mass.) is one gastric stent made of a Nitinol shape memory alloy. Other examples of gastric sleeves and stents may be seen in PCT Publication WO 03/094785 A1 to Egan; U.S. Pat. App. Pub. 2004/0092892 A1 to Kagan et al.; and U.S. Pat. App. Pub. 2004/0107004 A1 to Levine et al., each of which is incorporated herein by reference in its entirety.

Figure 7:
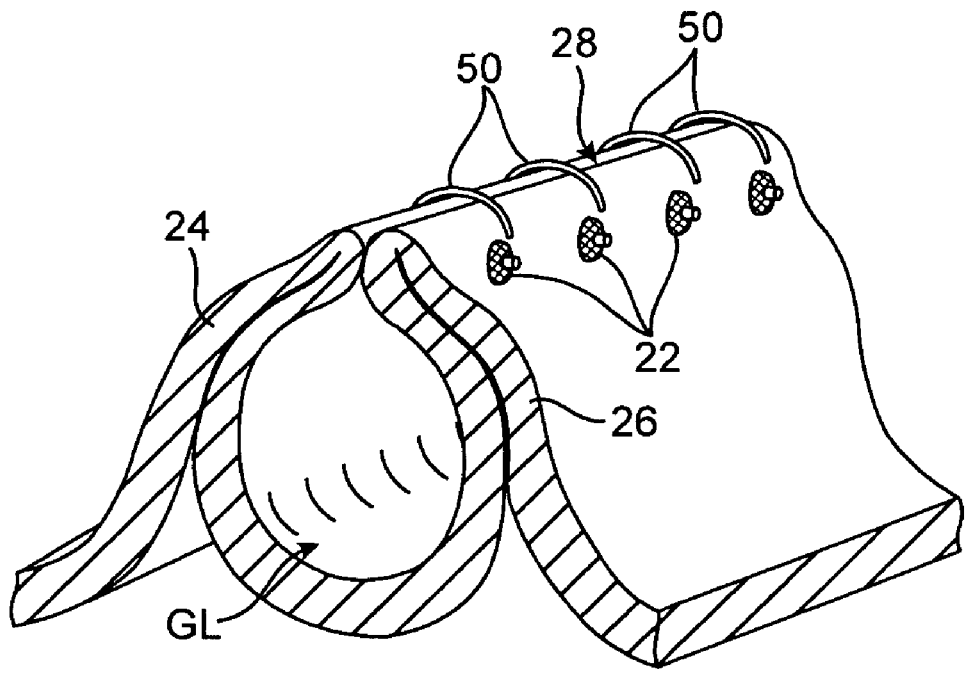
FIG. 7 shows a partial perspective view of a gastric lumen secured via expandable anchors and further buttressed via a suture oversew which may be utilized for alleviating pressure upon the joined tissue regions immediately adjacent the anchors.

FIG. 7 shows a partial perspective cross-sectional view of approximated tissue folds 24, 26 which may be secured utilizing several tissue anchors 22 secured via lengths of suture to complementary anchors on the opposing sides of tissue folds 24, 26. A second row of clips or sutures 50 is shown as an oversew (intermittent or running) which may help secure the tissue folds 24, 26 to one another to facilitate the tissue adhesion along the joined length of approximated tissue. The region of approximated tissue below oversew 50 along tissue interface 28 where tissue folds 24, 26 are fastened by tissue anchors 22 may act as a barrier to fluctuating pressures imparted from gastric lumen GL or other environmental fluctuations.

Figure 8A:
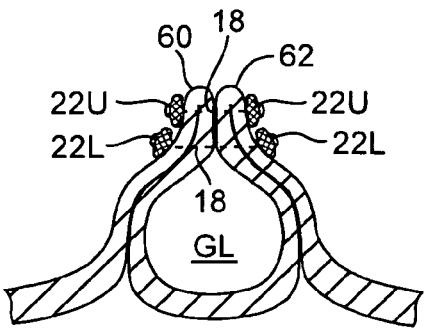
FIGS. 8A and 8B show a cross-sectional side views of another example where pressure exerted by the gastric lumen and ultimately experienced by the joined ridges of tissue may be mitigated via a double-row of deployed tissue anchors.
Figure 8B:
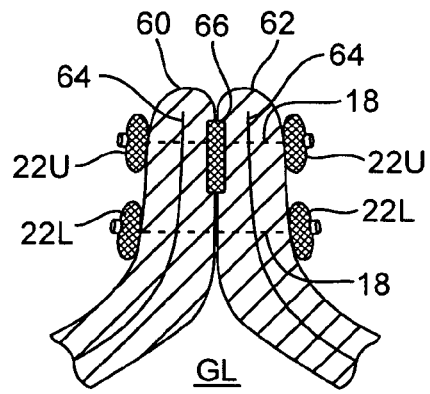

Another example of securing approximated tissue folds to one another is shown in the cross-sectional view of gastric lumen GL in FIG. 8A. First tissue fold 60 may be seen secured to second tissue fold 62 via at least two adjacent rows of tissue anchors 22U, 22L mimicking an oversew to form gastric lumen GL. As seen, the tissue anchors 22U, 22L are held to one another via lengths of suture 18. FIG. 8B shows a detail view from FIG. 8A of the region between joined tissue folds 60, 62. As mentioned above, the pair of lower tissue anchors 22L immediately adjacent gastric lumen GL may function to attenuate or eliminate fluctuating pressures, pH, etc., from gastric lumen GL while the pair of upper tissue anchors 22U may be utilized to adhere the tissue folds 60, 62 to one another along adhered tissue region 66, which is located above the tissue joined via lower tissue anchors 22L, in this example.

Tissue folds 60, 62 are desirably folded and joined to one another such that they have serosa-to-serosa contact 64 within each fold. The lengths of wire or suture 18 securing tissue anchors 22U, 22L to one another desirably passes through the serosa-to-serosa contact 64 region of each fold.

To further facilitate tissue adhesion between the contacting tissue folds 60, 62, the entire length of tissue region 66 along gastric lumen GL or discrete areas of tissue region 66 along gastric lumen GL may be injured via a number of methods. Injuring the apposed tissue along joined tissue region 66 may ultimately promote healing of the contacting tissue between the folds when maintained in uninterrupted contact via upper tissue anchors 22U. Such healing may comprise remodeling of the tissue folds 60, 62 along the regions of apposed tissue contact to facilitate prolonged maintenance of the folds. During the period of time necessary for remodeling/scar tissue formation, the tissue anchors 22U may be utilized to maintain, e.g., temporarily maintain, contact of the injured tissue along each tissue fold. The tissue anchors 22U, 22L optionally may be removed or may biodegrade ultimately upon formation of scar tissue. Alternatively, the anchors may be left in place indefinitely to reinforce the scar tissue and ensure prolonged maintenance of the tissue folds 60, 62.

As mentioned above, the tissue region may be injured through any number of methods. One example for locally injuring the tissue may be to utilize electrical or radio-frequency energy applied via a probe. Tools and methods are described in further detail in U.S. Pat. App. Pub. U.S. 2004/0034371 A1 to Lehman et al., which is incorporated herein by reference in its entirety. Additional methods and tools for injuring and/or removing the tissue are also described in further detail in U.S. patent application Ser. No. 10/898,683 filed Jul. 23, 2004, which is also incorporated herein by reference in its entirety.

Moreover, aside from injuring the tissue via electrical or radio-frequency energy, the top layer of tissue, i.e., the mucosal layer, may be removed through a variety of methods to reveal the underlying muscularis layer, which may then be apposed into contact along tissue region 66, as shown in FIG. 8B. Optionally, opposing regions of tissue to be joined may have strip mucosectomies performed on then. The opposing tissue folds 60, 62 may then be formed and approximated to bring the denuded regions of tissue along tissue region 66 into contact. Methods and tools for performing mucosectomy and joining apposed folds of tissue are described in further detail in U.S. patent application Ser. No. 10/954,658 filed Sep. 29, 2004, which is incorporated herein by reference in its entirety.

Figures 9A, 9B:
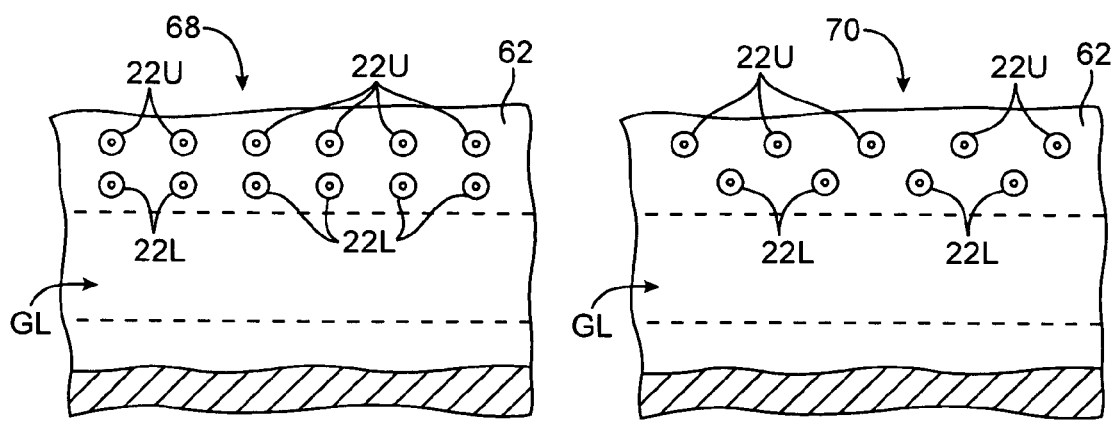
FIG. 9A shows a side view of one example for tissue anchor deployment where the double-row of tissue anchors may be positioned adjacent to one another along the tissue ridge.
FIG. 9B shows a side view of another example where the double-row of tissue anchors are positioned in a staggered manner.

To form the adjacent rows of tissue anchors along the joined tissue folds 60, 62, the anchors may be positioned relative to one another in various ways. For instance, FIG. 9A shows one example in which the tissue anchors may be positioned in an adjacent linear pattern 68 where a row of upper tissue anchors 22U may be aligned with a row of lower tissue anchors 22L such that each anchor is directly adjacent to one another. In another example, the anchors may be placed in a staggered pattern 70 where the anchors in the row of upper tissue anchors 22U may be staggered relative to the anchors in the row of lower tissue anchors 22L, as shown in FIG. 9B. In another variation, a single gastric lumen GL may have a combination of the linear arrangement 68 and staggered arrangement 70 of the tissue anchors along its length, if so desired.

Figure 9C:
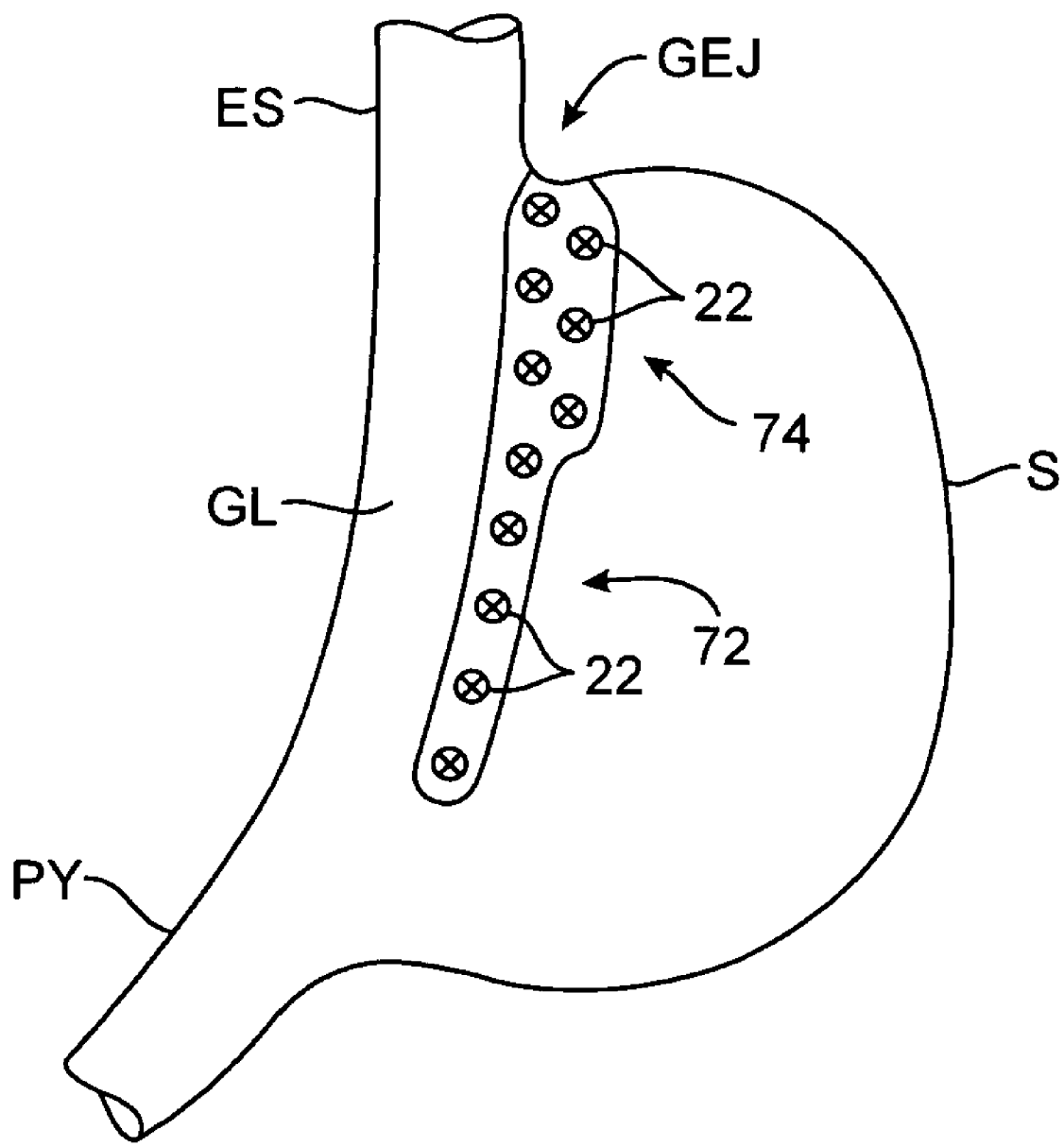
FIG. 9C shows yet another example in which a double-row of tissue anchors may be deployed along the tissue ridge adjacent to the gastroesophageal junction to alleviate pressure exerted by food or liquid when initially entering the stomach.

In yet another variation, a double row of tissue anchors 22 may be placed along only a portion of gastric lumen GL to maintain the integrity of the lumen GL. An example is shown in FIG. 9C in which gastric lumen GL may be reinforced with a dual anchor arrangement 74 (linear or staggered or a combination thereof) beginning from the gastroesophageal junction GEJ and extending at least partially towards pylorus PY. The portion of gastric lumen GL closest to the GEJ may be reinforced with a dual row arrangement to buttress the approximated tissue and to attenuate the increased pressure rise resulting from food or liquids initially entering the gastric lumen GL. The remainder of gastric lumen GL may be secured with a single anchor arrangement 72 as the pressure increase from the ingested food or liquid may not be as great within the distal lower portions of gastric lumen GL.

Figure 10A:
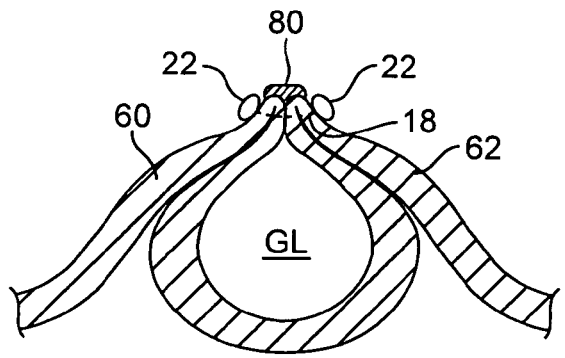
FIGS. 10A to 10D show cross-sectional views of another method for alleviating pressures exerted by the gastric lumen by utilizing biocompatible adhesives placed above, below, between, or throughout the formed tissue folds, respectively.

Aside from utilizing multiple rows of tissue anchors to attenuate or isolate environmental fluctuations from the approximated tissue folds, another method may include the placement of biocompatible adhesives along or around the adhesion regions between the tissue folds. Many commercially available biocompatible adhesives may be utilized; for instance, one such adhesive is BioGlue® Surgical Adhesive (Cryolife, Inc., Kennesaw, Ga.) which is a two-component surgical adhesive composed of purified bovine serum albumin and glutaraldehyde. Such a bio-adhesive 80 may be applied, in one variation, above the secured tissue folds 60, 62, as shown in FIG. 10A. In such a configuration, the adhered tissue below the adhesive 80 may be maintained in prolonged contact to facilitate the healing process.

Figure 10B:
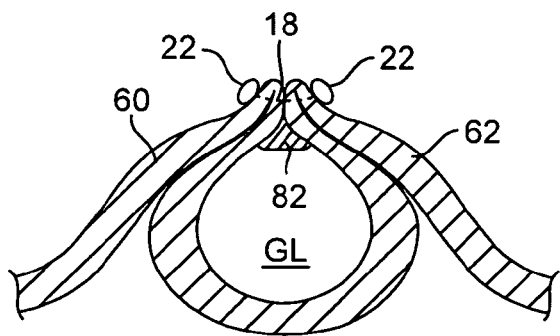
Figure 10C:
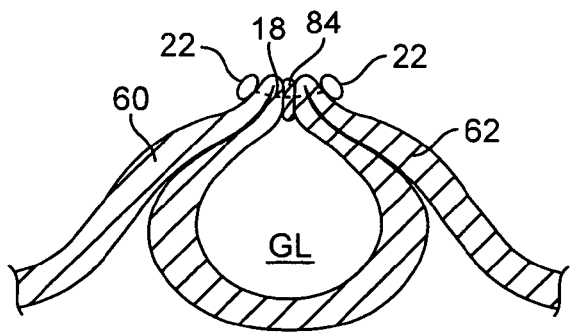
Figure 10D:
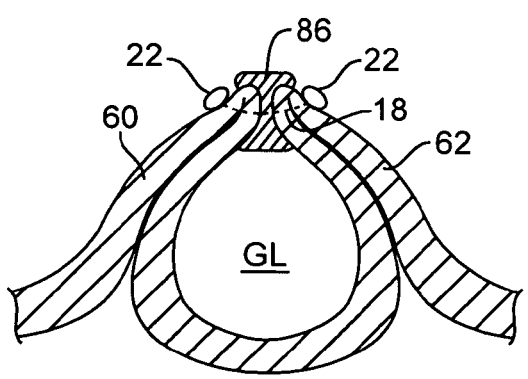
Figure 11:
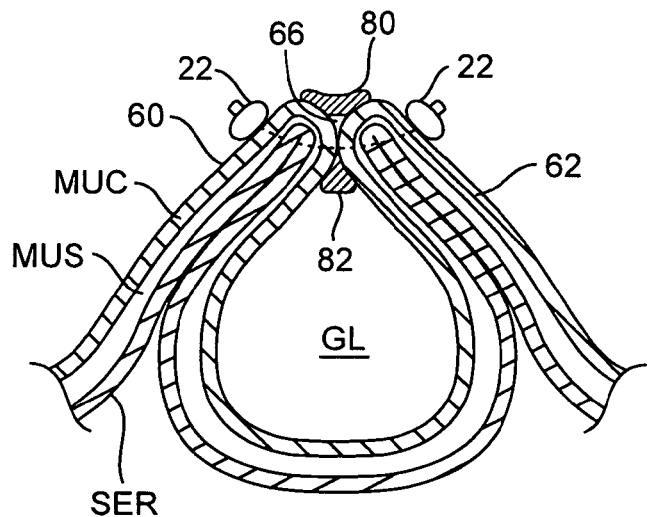
FIG. 11 shows a cross-sectional view of adhered tissue folds with adhesive applied above and below the joined tissue regions which may have their mucosal layers resected for fostering tissue adhesion.

Another configuration may include dispensing of bio-adhesive 82 between tissue folds 60, 62 below the tissue anchors 22 within gastric lumen GL, as shown in FIG. 10B. In this configuration, the bio-adhesive 82 may act to attenuate or isolate the secured tissue between tissue anchors 22. Yet another example may be seen in FIG. 10C where bio-adhesive 84 may be dispensed directly between tissue folds 60, 62. And yet another example may be seen in FIG. 10D in which bio-adhesive 86 may be dispensed not only between tissue folds 60, 62, but also above and below to buttress the tissue adhesion by tissue anchors 22.

The use of bio-adhesives may, of course, be utilized in combination with other environmental attenuation or isolation securement methods described herein. For instance, bio-adhesives may be used to isolate the adhered and secured region of tissue 66 where tissue folds 60, 62 have had their mucosal layers removed, as described above. Shown in FIG. 1, the approximated tissue is shown in further detail where the mucosal layer MUC may be seen along with the underlying muscularis layer MUS and serosal layer SER. The apposed tissue region 66 may be seen as having been denuded of its mucosal layer MUC such that the underlying muscularis layers MUS of their respective tissue folds 60, 62 are held in contact against one another. Bio-adhesives may be dispensed both above 80 and below 82 the apposed and denuded tissue region 66, as shown, to effectively isolate the tissue region 66 to promote healing. The adhesive may be optionally dispensed above 80 or below 82, or even between apposed tissue region 66 in other variations.

Figure 12:
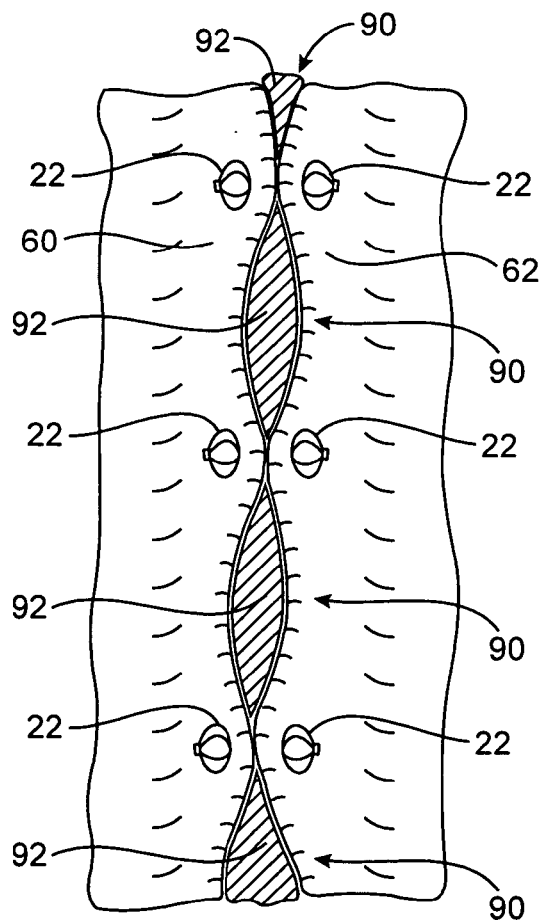
FIG. 12 shows a top view of the gastric lumen where adhesive may be filled between adjoining tissue folds in-between the tissue anchors for alleviating pouch pressures as well as forming a tight seal between the tissue ridges.

In another use, bio-adhesive 92 may optionally be dispensed along the apposed tissue folds 60, 62 within gaps 90 along the tissue contact region in the areas in-between the tissue anchors 22, as shown in the top view of apposed tissue folds 60, 62 of the gastric lumen in FIG. 12. Gaps 90, which have been exaggerated for illustrative purposes, may or may not form along the apposed tissue in-between tissue anchors 22 depending upon numerous factors. For instance, if tissue anchors 22 were positioned relative to one another at extended distances, gaps 90 may possibly form between tissue anchors 22. In any case, whether gaps 90 are present or absent along the tissue ridge in-between tissue anchors 22, bio-adhesive 92 may be dispensed in the areas, as shown, between the apposed tissue folds 60, 62 along the tissue ridge to seal gastric lumen GL along its length and to facilitate the tissue adhesion process.

Various tools may be utilized for endoscopically dispensing bio-adhesives along or between a formed gastric lumen GL. One variation of a tool is shown in the illustrative assembly of FIG. 13. In this variation, a conventional endoscope 100 having a working lumen 112 may be utilized by advancing it into the stomach of a patient who has had a gastric lumen GL formed within the patient's stomach. The endoscope 100 may be advanced per-orally and transesophageally into the formed gastric lumen GL. Alternatively, a percutaneous approach may be utilized rather than an endoluminal one, in which case endoscope 100 or a laparoscopic tool may be advanced transgastrically into the stomach to provide access to the gastric lumen GL.

Figure 13:
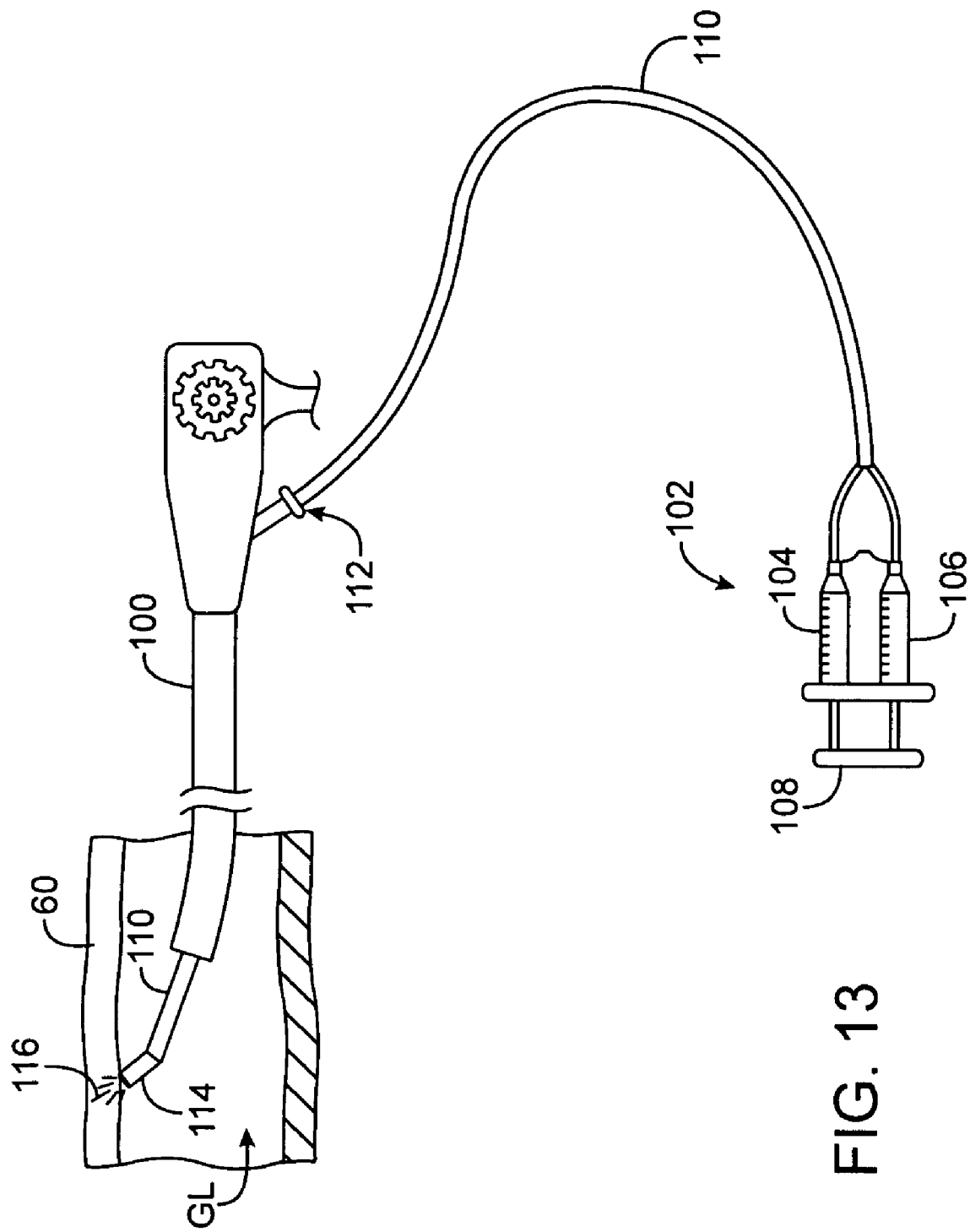
FIG. 13 shows one example of a device which may be utilized to endoscopically dispense the biocompatible adhesives along the gastric lumen.

The example of FIG. 13 shows a flexible endoscope 100 but is intended to be merely illustrative. As shown, once endoscope 100 has been advanced into or through gastric lumen GL, a bio-adhesive dispensing assembly 102 having first and second dispensing containers or syringes 104, 106, respectively, and a common plunger 108 may be connected to a flexible or rigid delivery tube 110, which may be advanced either directly into gastric lumen GL or through working lumen 112 of endoscope 100. Depending upon how many separate containers or syringes are necessary for forming the bio-adhesive, dispensing assembly 102 may be adjusted accordingly and delivery tube 110 may be formed or extruded to have the requisite number of delivery lumens in fluid communication with a respective syringe.

The distal tip of delivery tube 110 may have a mixing tip or chamber 114 in which the separate components disposed within the separate syringes may be combined to form an active bio-adhesive. As plunger 108 is actuated by the surgeon or practitioner, the contents of syringes 104, 106 may be combined within mixing tip 114 and dispensed as bio-adhesive 116 along or within the tissue ridge of gastric lumen GL. The position of mixing tip 114 may be manipulated by moving endoscope 100, if used, moving delivery tube 110, or both along or through gastric lumen GL.

Figure 14:
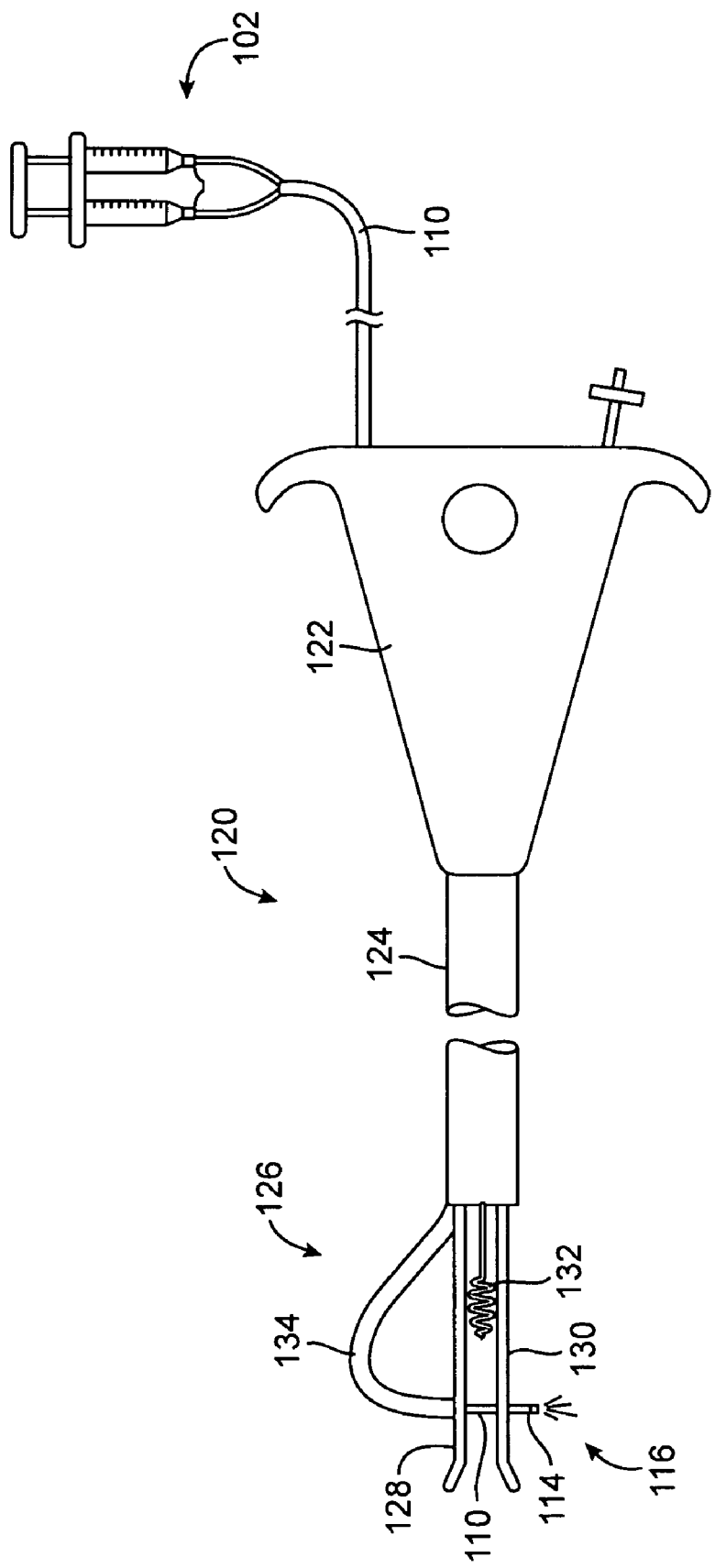
FIG. 14 shows another example of a device which may be utilized for forming the gastric lumen and dispensing the biocompatible adhesive.

In another variation for dispensing the bio-adhesive, dispensing assembly 102 may be used in combination with a device utilized for forming and/or securing the tissue folds. FIG. 14 shows an example of a tissue approximation and securement assembly 120 having a handle 122 and an elongate member 124 extending from the handle 122. Elongate member 124 may be optionally rigid or flexible depending upon the approach. For example, if elongate member is advanced per-orally and trans-esophageally into a patient's stomach, elongate member 124 may be flexible; alternatively, if advanced percutaneously and trans-gastrically into the stomach, elongate member 124 may be rigid as a laparoscopic tool.

Examples and variations of tissue approximation and securement assembly 120 are described in further detail in U.S. patent application Ser. No. 10/954,666 filed Sep. 29, 2004, which is incorporated herein by reference in its entirety. One example of tissue approximation and securement assembly 120 is also described briefly below.

Tissue approximation and securement device 126 may be attached or extend from the distal end of elongate member 124 and may generally comprise upper and lower extension members 128, 130, respectively. Extension members 128, 130 may project distally from the end of elongate member 124 and have a slidable and rotatable tissue engagement member 132, e.g., a corkscrew-like tissue engager, configured to be positioned between the extension members 128, 130. In operation, tissue engagement member 132 may be urged distally of extension members 128, 130 to adhere the tissue thereto. Engagement member 132 may then be pulled proximally back between extension members 128, 130 such that the engaged tissue is also pulled proximally and sandwiched between extension members 128, 130. Before the tissue is engaged or even after, launch tube 134 may be actuated such that a distal portion of the launch tube 134 is aligned transversely relative to the engaged tissue.

Launch tube 134, which may comprise a hollow tubular member, may typically have a needle and securement assembly disposed within. The needle and securement assembly may be removed from launch tube 134 and bio-adhesive delivery tube 110 of adhesive dispensing assembly 102 may be passed therein. With tissue approximation and securement device 126 positioned within or adjacent to gastric lumen GL, mixing tip or chamber 114 may be advanced out of launch tube 134 and dispensing assembly 102 may be actuated to dispense the bio-adhesive 116 into or along the appropriate tissue areas.

Figure 15:
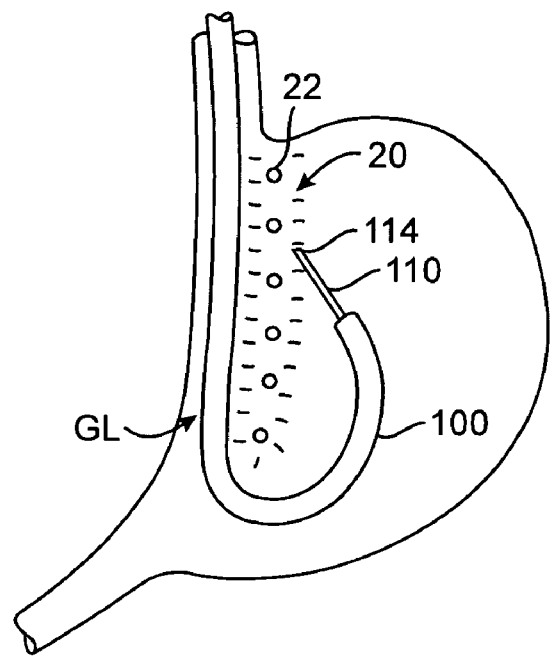
FIGS. 15 and 16 illustrate exemplary methods on how adhesive may be dispensed along the gastric lumen using a manipulatable endoscopic device.

In positioning the mixing tip or chamber 114, one approach is shown in FIG. 15. A conventional endoscopic device 100 or a shape-lockable endoscopic device, as described in U.S. Pat. No. 6,790,173, which is incorporated herein in its entirety, may be passed through the formed gastric lumen GL and then retroflexed such that the distal end is adjacent to the tissue ridge 20. The delivery tube 110 may be urged distally out of endoscopic device 100 until mixing tip or chamber 114 is desirably positioned relative to tissue ridge 20 for dispensing the bio-adhesive from outside gastric lumen GL.

Figure 16:
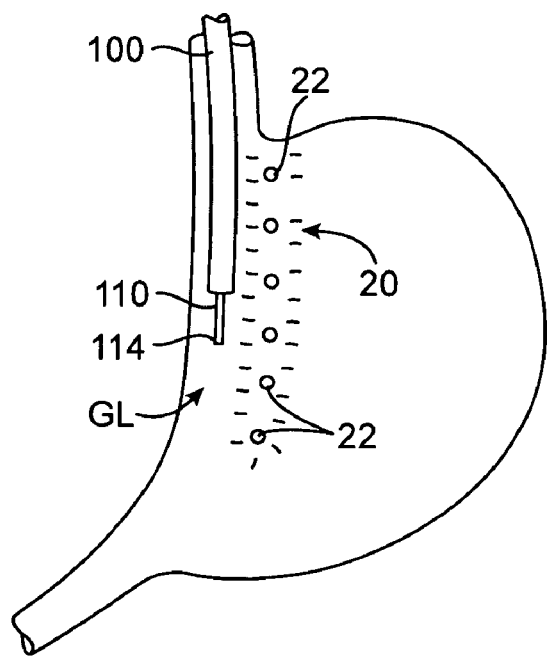

Alternatively, endoscopic device 100 may be advanced only partially into gastric lumen GL, as shown in the example of FIG. 16, and delivery tube 110 may then be urged distally out of endoscopic device 100 such that the bio-adhesive may be dispensed against or along tissue ridge 20 from within gastric lumen GL. Either method may be utilized alone or in combination with one another to dispense the bio-adhesive anywhere along, outside, or within tissue ridge 20 relative to gastric lumen GL.

Figure 17:
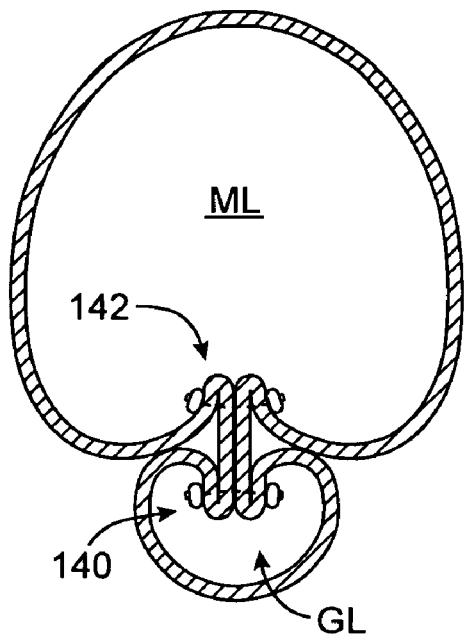
FIG. 17 shows a cross-sectional view of a stomach which may be approximated such that the formed gastric lumen is buttressed by additional adjoined tissue folds adjacent to the gastric lumen.

Aside from the use of bio-adhesives, the tissue regions within the stomach may themselves be arranged and plicated in such a way as to facilitate the alleviation of pressures and other environmental fluctuations from the adhered and secured regions of tissue forming gastric lumen GL. FIG. 17, for instance, shows one variation in the top cross-sectional view of a stomach having a first anchor securement assembly 140 securing two tissue folds extending into gastric lumen GL. These folds extend partially into the separated main lumen ML and are also used to form an additional adjacent plication using a second anchor securement assembly 142. Thus, the two adjacent sets of tissue folds utilize common folds of tissue in a back-to-back manner. This manner of adhering and securing the tissue folds may effectively isolate the region of tissue between the respective tissue securement assemblies 140, 142 from environmental fluctuations.

Figure 18:
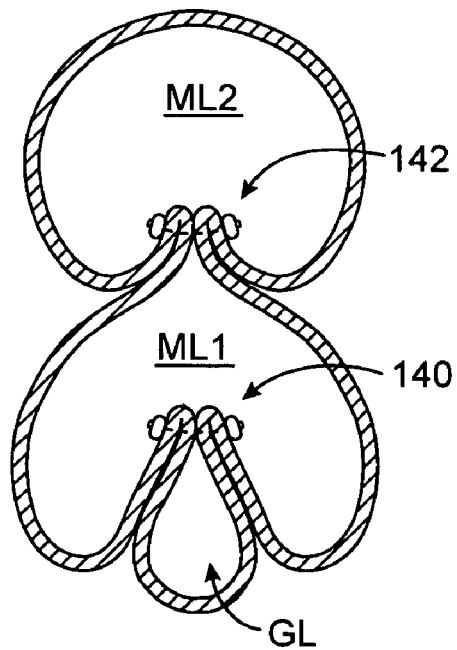
FIG. 18 shows a cross-sectional view of a stomach in which additional tissue folds may be approximated within the gastric space of the stomach adjacent to the gastric lumen.

FIG. 18 shows another example in which a first anchor securement assembly 140 may be used to secure a first set of tissue folds to form a gastric lumen GL, as described above. A second anchor securement assembly 142 may then be used to approximate and secure regions of tissue from within the main lumen to further divide the main lumen into a first main lumen ML1 and second main lumen ML2. The size of the first and second main lumens ML1, ML2 may be varied depending upon the size of the second set of folds and proximity in relation to the first set of folds forming gastric lumen GL. Moreover, the second set of folds may be secured such that they are immediately adjacent to or directly lie upon the first set of folds. Such a configuration may effectively isolate the approximated tissue folds of gastric lumen GL from the fluctuations experienced by the remaining stomach.

Figure 19:
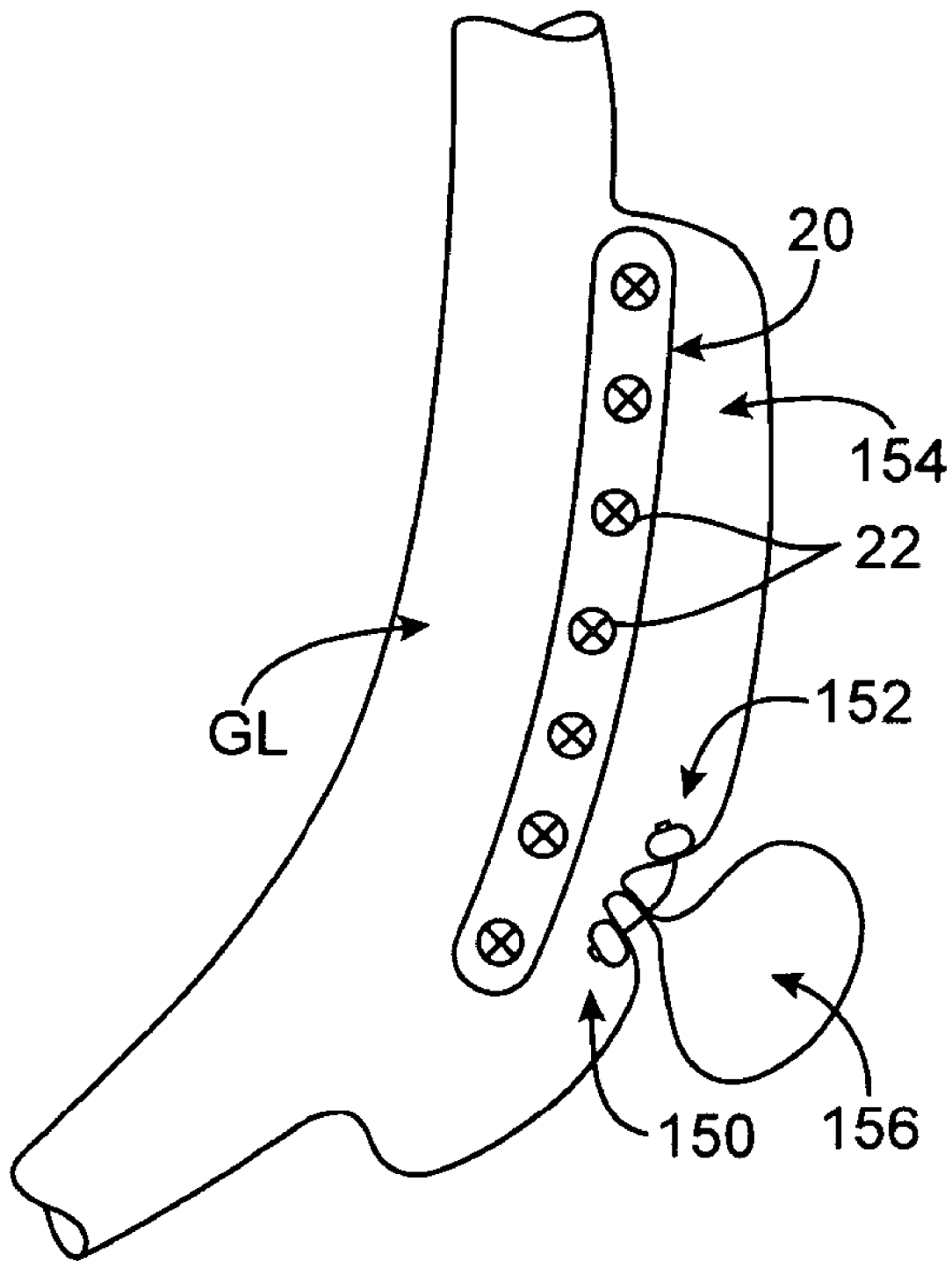
FIG. 19 illustrates a side view of a stomach with its fundus joined to the antrum region to alleviate pressure seen by the approximated tissue folds of the gastric lumen.

Yet another variation is shown in FIG. 19 which shows a stomach that has had a gastric lumen GL formed, as above, with the addition of a fundus-to-antrum tissue approximation 150, i.e., the tissue from the fundus is approximated and secured to the tissue from the antrum with an anchor securement assembly 152. This has a similar effect from the variation shown in FIG. 18 above in that the main lumen 154 of the excluded stomach is further reduced substantially. A resulting portion of stomach 156 may result from the fundus-to-antrum approximation.

Another variation may be seen in FIGS. 20A and 20B, which show a cross-sectional side view of another method for approximating and securing tissue folds. As shown in FIG. 20A, a compressible first tissue anchor 160 may be deployed relative to tissue fold 24 in a first direction. Suture 18 may be seen attached to first anchor 160 and passing through anterior tissue fold 24 and looped over the fold 24 to extend through posterior tissue fold 26 and through second anchor 162.

As the two anchors 160, 162 and respective tissue folds 24, 26 are approximated towards one another, tissue fold 24 may be seen to evert relative to tissue fold 26 due to the positioning of anchors 160, 162. The approximated tissue folds 24, 26 may be secured to one another via a uni-directional cinch 164. The overlapping region of tissue may facilitate the adhesion of the tissue folds 24, 26 because of the overlap configuration. The shear forces required to separate the two folds help with the tissue adhesion process. Examples of expandable or reconfigurable tissue anchors and unidirectional cinches may be seen in further detail in U.S. patent application Ser. No. 10/840,950 filed May 7, 2004, which is incorporated herein by reference in its entirety.

Another variation is shown in FIGS. 21A and 21B, which shows how tissue anchors 160, 162 may be deployed such that they are apposed to one another relative to their respective tissue folds 24, 26. The length of suture 18 connecting the two anchors may be deployed such that it loops over the tissue folds 24, 26 and comes back through the folds 24, 26. Approximation of the folds 24, 26 and the anchors 160, 162 may be accomplished by pulling on the terminal end of suture 18 until the folds 24, 26 invert relative to one another and are brought together. The folds 24, 26 may be secured in this inverted manner by forcing cinch 164 distally to lock the relative positions of tissue anchors 160, 162. The resulting gastric lumen GL has the tissue anchors 160, 162 positioned within gastric lumen GL and the tissue folds 24, 26 secured to one another in an inverted manner.

Figure 22A:
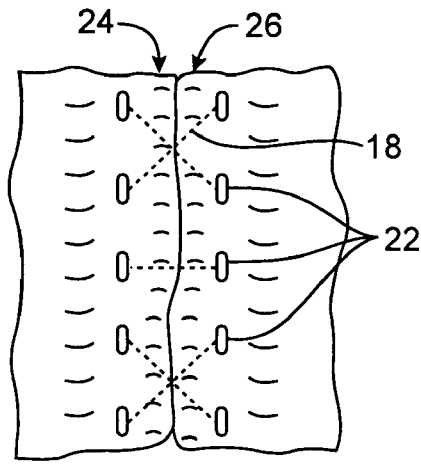
FIGS. 22A to 22C show variations in anchor placements which cross one another to create regions of adhesion isolated from fluctuations.
Figure 22B:
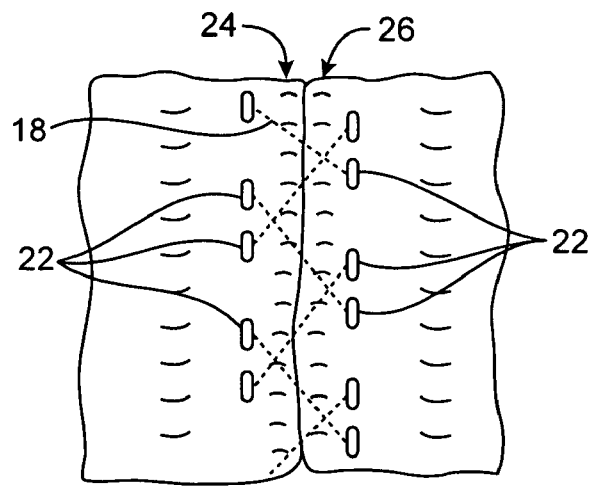
Figure 22C:
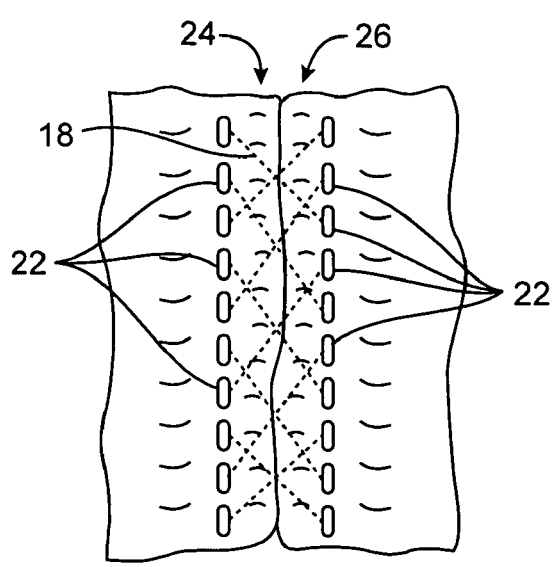

Yet another configuration is shown in FIG. 22A, which shows a top view of approximated and secured tissue folds 24, 26. As shown, the tissue anchors 22 may be connected to one another such that the lengths of suture 18 are in a crossing configuration relative to one another. Tissue anchors 22 may be paired to form discrete sets of crossed sutures. Alternatively, the tissue anchors 22 may be paired to form staggered and interconnected crossed sutures, as shown in FIG. 22B. In another variation, crossed pairs of tissue anchors 22 may be interconnected with adjacent tissue anchors 22 such that the anchors are interconnected along the length of the approximated tissue folds 24, 26 forming gastric lumen GL. In any of these variations, the crossed tissue anchors 22 may be utilized along the entire lengths of the gastric lumen GL or only along portions thereof. The crossed suture configuration may allow for the tight approximation and securement of the tissue folds 24, 26, thereby helping to facilitate the tissue adhesion between the folds.

Figure 23:
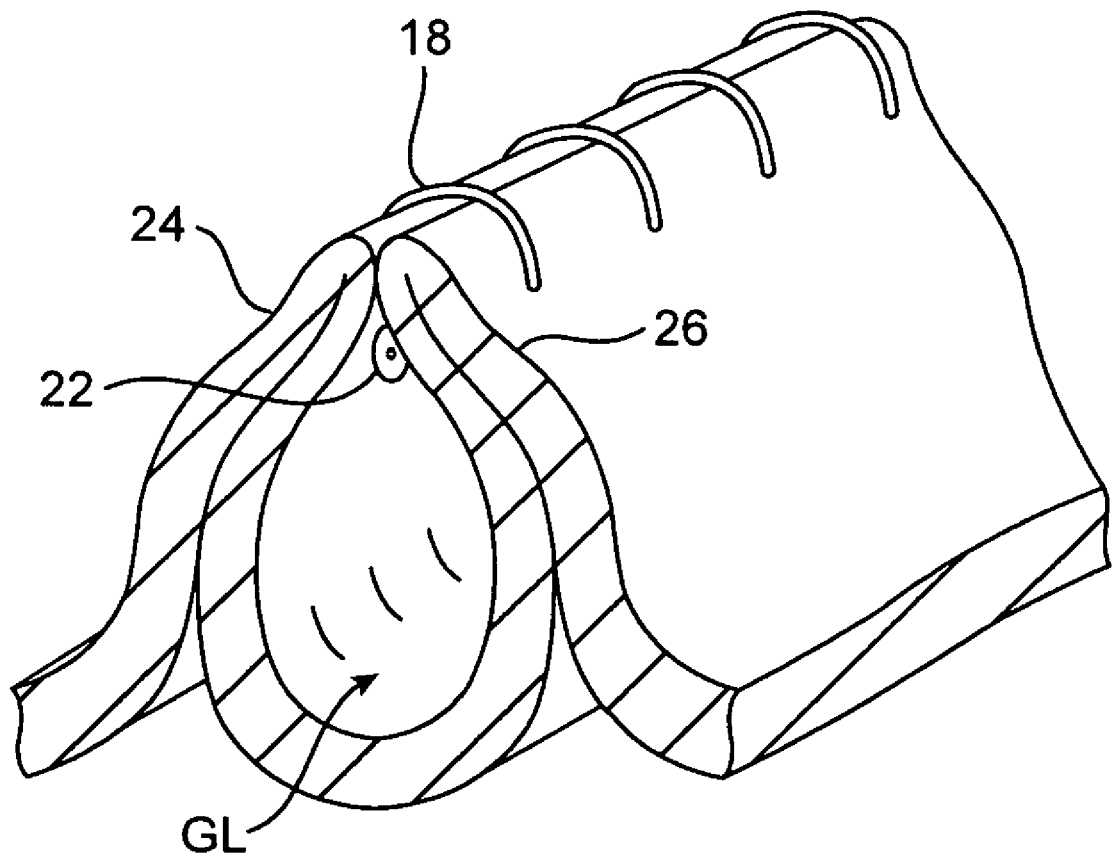
FIG. 23 shows yet another variation utilizing tissue anchors positioned within the gastric lumen and having sutures overlying across the tissue folds to simulate an oversew.

FIG. 23 shows yet another variation in the partial perspective view of approximated tissue folds 24, 26 which are secured with deployed tissue anchors 22 positioned within gastric lumen GL and with lengths of suture 18 looping over the approximated tissue folds 24, 26 to simulate a suture oversew. The looped portions of suture 18 may help with tissue adhesion by simulating the effects of a suture-based oversew to facilitate the adhesion of the tissue folds 24, 26 to isolate the adhered tissue regions and to attenuate the effects of environmental fluctuations from food passage through the gastric lumen GL as well as from the remaining excluded stomach.

Figure 24A:
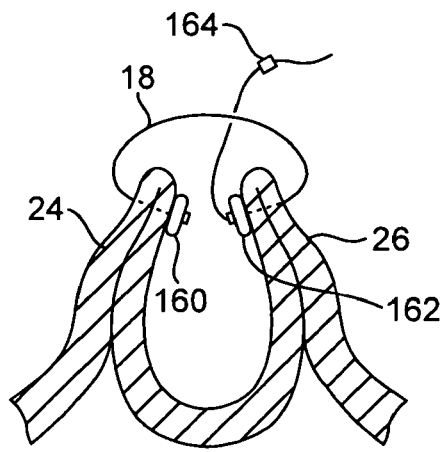
FIGS. 24A and 24B illustrate yet another variation in which the tissue anchors are positioned within the gastric lumen and approximated towards one another with a cinch to simulate an oversew on the tissue folds.
Figure 24B:
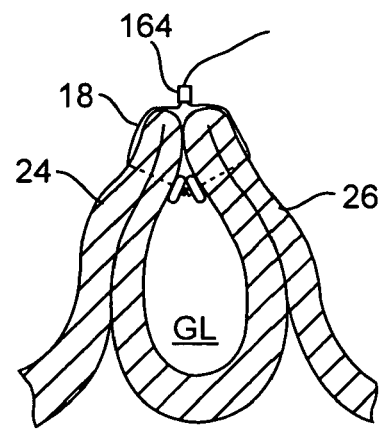

FIGS. 24A and 24B show cross-sectional views of one example for simulating a suture oversew utilizing deployable tissue anchors. Similar to the anchor deployment shown in FIG. 21A, first and second tissue anchors 160, 162 may be deployed such that they are in apposition to one another in their respective tissue folds 24, 26. Suture 18 may be looped over the tissue and the terminal end of suture may extend from second anchor 162. As the terminal end of suture 18 is pulled between the folds of tissue 24, 26 and the anchors are drawn to one another, suture 18 may overlie the tissue folds 24, 26 much like a suture oversew as cinch 164 helps to maintain the anchor positions relative to one another, as shown in FIG. 25B. In this case, the tissue remains in contact with one another rather than inverting into gastric lumen GL.

Figure 25A:
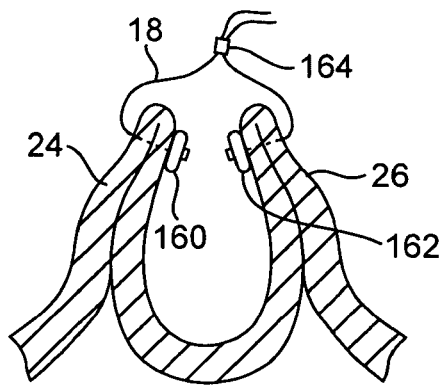
FIGS. 25A and 25B show yet another variation similar to that of FIGS. 24A and 24B.
Figure 25B:
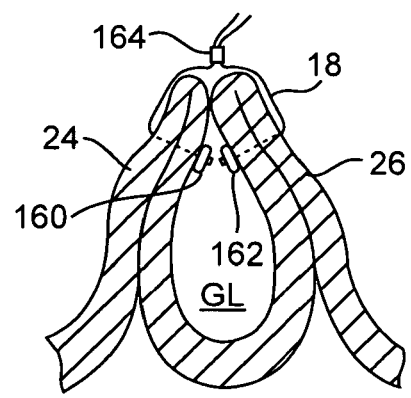

In another variation shown in FIGS. 25A and 25B, the anchors may be positioned similarly as above, however, each tissue anchor 160, 162 may attach to a terminal end of the suture. The other ends of the looped and overlying suture 18 may be routed through a cinch 164 such that when the cinch 164 is drawn relative to the suture 18, the anchors 160, 162 are drawn together and the tissue folds 24, 26 approximated into contact with one another, as shown in FIG. 25B. The cinch 164 may be drawn until the suture 18 overlying the tissue folds 24, 26 lie sufficiently close or tightly against the adhered tissue, much like a suture oversew.

Figure 26A:
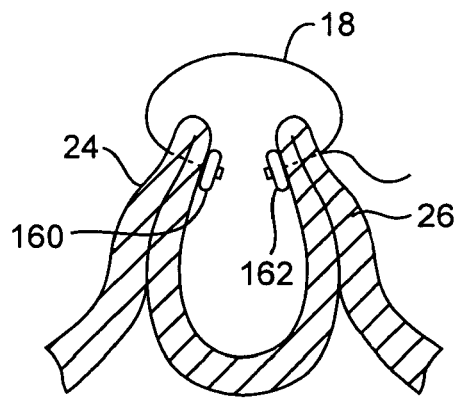
FIGS. 26A and 26B show yet another variation similar to that of FIGS. 24A and 24B.
Figure 26B:
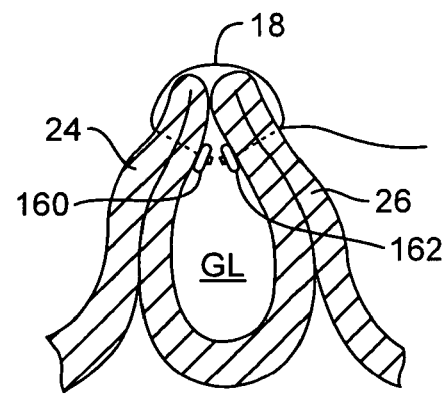

In yet another variation, the tissue anchors 160, 162 are deployed as above with respect to the tissue folds 24, 26, but the second tissue anchor 162 may have the length of suture 18 routed into and through the anchor 162 such that the suture passes back through the second tissue fold 26 a second time, as shown in FIG. 26A. To approximate the tissue folds 24, 26, the suture 18 may be drawn to pull the tissue anchors 160, 162 towards one another until the overlying suture 18 is drawn tightly against the tissue folds 24, 26 much like an oversew.

The method of simulating a suture oversew may be utilized to simulate a series of interrupted tissue oversew. It may also be utilized to form continuous or running lengths of suture along the tissue folds to simulate a continuous suture oversew.

Figure 27A:
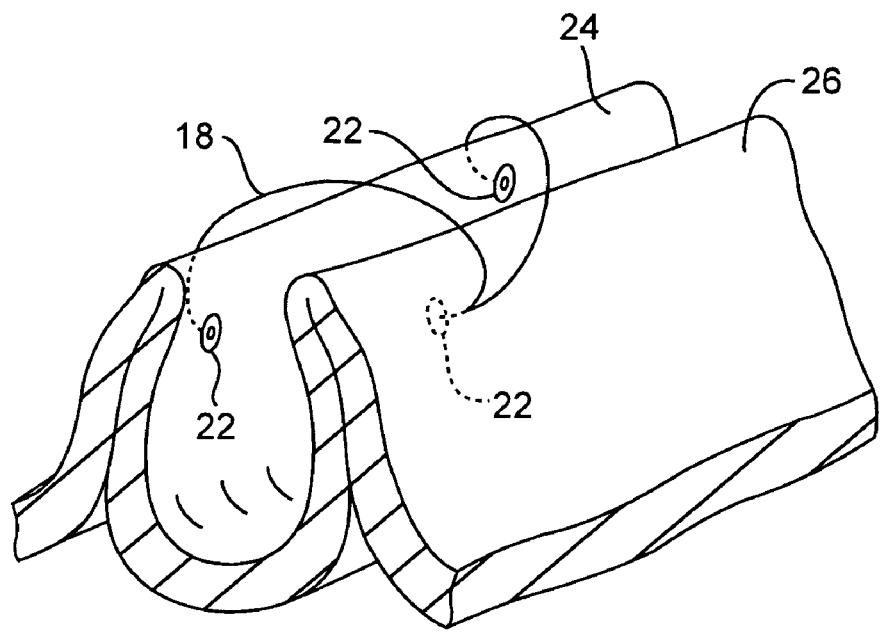
FIGS. 27A and 27B show a partial perspective view of tissue anchors which may be positioned within the gastric lumen and interconnected between several anchors similarly positioned to create a continuous oversew effect.
Figure 27B:
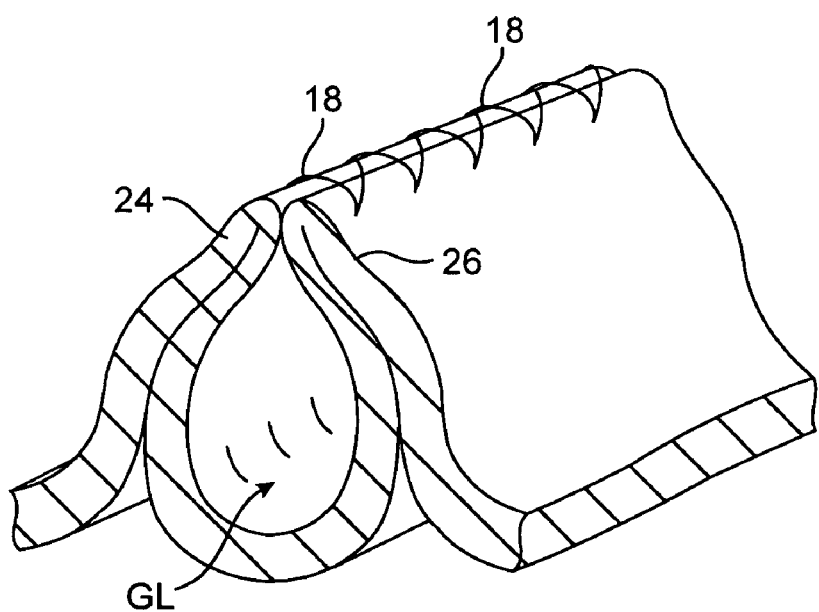

In one variation shown in the partial cross-sectional view of FIG. 27A, at least two or three tissue anchors 22 may be interconnected to one another with a single length of suture 18. Each anchor 22 may be deployed along tissue folds 24, 26 in a staggered manner such that suture 18 overlies the approximated tissue folds 24, 26 in a continuous oversew fashion. Although the example of FIG. 27A shows three interconnected anchors 22, a plurality of additional anchors may be interconnected in series such that when deployed along tissue folds 24, 26, the tightening of suture 18 overlying the tissue may form a continuous length of suture oversew, as shown in FIG. 27B.

Figure 28A:
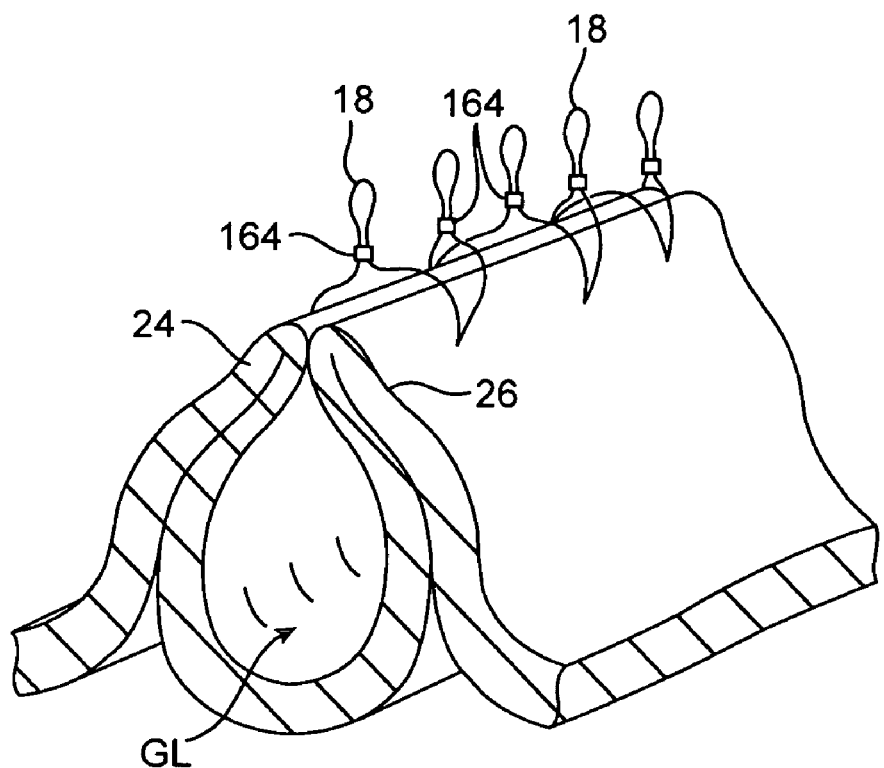
FIG. 28A show a partial perspective view of another variation for utilizing anchors positioned within the gastric lumen which are approximated to create a continuous oversew effect using cinches.
Figure 28B:
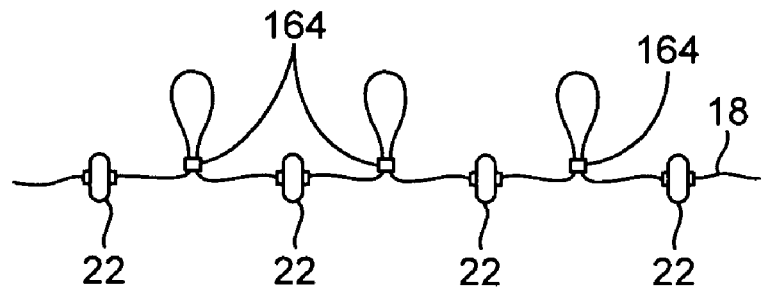
FIG. 28B shows an example of one tissue anchor assembly which may be utilized in the example of FIG. 28A and which may comprise several tissue anchors interconnected in series with intermediate cinches.

FIG. 28A shows another example of simulating a continuous suture oversew utilizing the anchor configuration of FIGS. 25A and 27A. In this variation, a number of tissue anchors 22 may be interconnected in series via a sufficient length of suture, as shown in FIG. 28B. A number of corresponding cinches 164 may be positioned on the suture 18 between each adjacent anchor 22. When deployed, each tissue anchor 22 may be positioned along the interior of gastric lumen GL in a staggered configuration such that the suture 18 crosses over the tops of tissue folds 24, 26 in a running oversew with the cinches 164 positioned above the tissue, as shown in FIG. 28A.

Figure 29A:
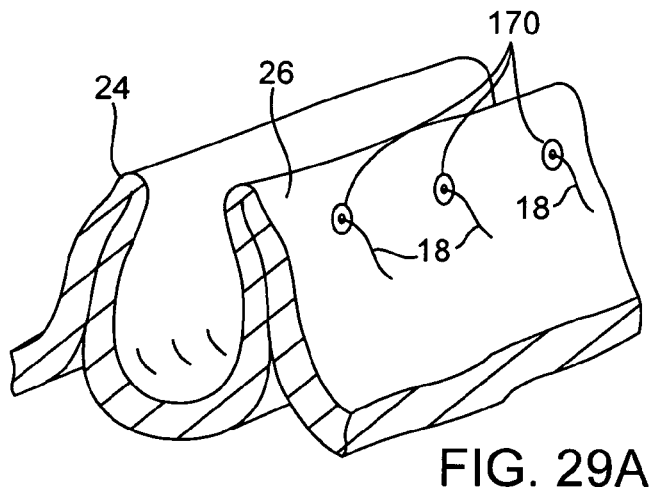
FIGS. 29A to 29C show partial perspective and top views, respectively, of yet another example utilizing tissue anchors positioned both within the gastric lumen and externally of the gastric lumen.
Figure 29B:
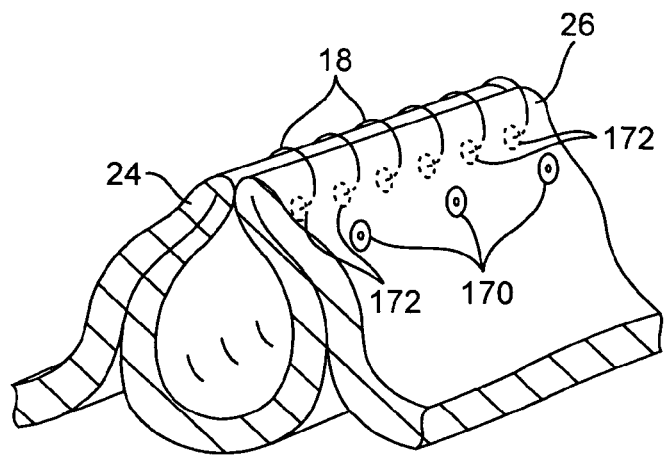
Figure 29C:
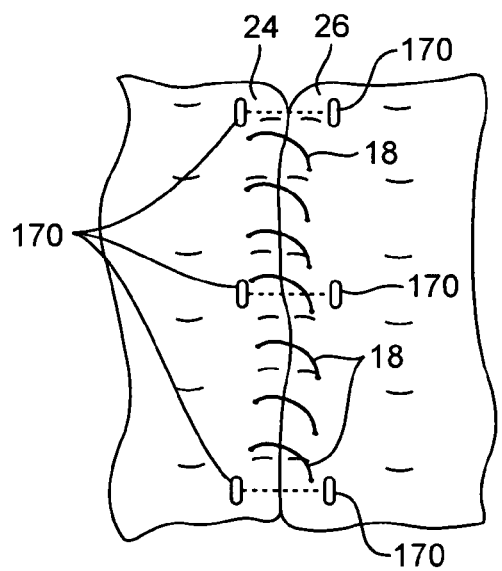

FIGS. 29A to 29C show yet another variation in which tissue anchors may be utilized positioned both exteriorly and interiorly of gastric lumen GL. As shown in the perspective view of FIG. 29A, one or more tissue anchors 170 may be deployed exteriorly of the gastric lumen GL to be formed. These exterior tissue anchors 170 may be drawn together to loosely approximate the tissue folds 24, 26. As shown in FIG. 29B, a number of additional tissue anchors 172 may then be deployed interiorly of gastric lumen GL such that the suture 18 forms a suture oversew. The interior tissue anchors 172 may be tightened to further approximate and adhere the tissue folds 24, 26 to one another. The oversew may be interrupted or continuous and it may utilize any of the oversew configurations described herein. Moreover, this combination of different anchoring methods may be utilized with any of the anchoring configurations described herein. FIG. 29C shows a top view of one variation of a resulting tissue approximation utilizing the tissue anchoring combination of FIGS. 29A and 29B. As shown, the exterior tissue anchors 170 may be placed intermittently along tissue folds 24, 26 to loosely hold the tissue against one another. The interior tissue anchors 172 may then be utilized to simulate the tissue oversew, as described herein, to draw the tissue into an adhesion region isolated from the environmental fluctuations.

Although a number of illustrative variations are described above, it will be apparent to those skilled in the art that various changes and modifications may be made thereto without departing from the scope of the invention. Moreover, although specific configurations and applications may be shown, it is intended that the various features may be utilized in various types of procedures in various combinations as practicable. It is intended in the appended claims to cover all such changes and modifications that fall within the true spirit and scope of the invention.

What is claimed is:

1. A method of isolating an approximated region of tissue within a stomach, comprising:

securing, from within the stomach, a first fold of tissue to a second fold of tissue using a first plurality of tissue anchor assemblies along an interface between the first and second folds of tissue such that a gastric lumen is formed between the first and second folds of tissue, the gastric lumen extending substantially from a gastroesophageal junction of the stomach to at least partially toward a pylorus of the stomach, with each of the first plurality of tissue anchor assemblies including a first tissue anchor engaging a surface of the first fold of tissue outside of the gastric lumen, a second tissue anchor engaging a surface of the second fold of tissue outside of the gastric lumen, and a connector extending through each of the first fold of tissue and the second fold of tissue, without looping over either of the first fold of tissue or the second fold of tissue, to connect the first tissue anchor with the second tissue anchor; and reinforcing the interface between the first and second folds of tissue in the gastric lumen using a second plurality of tissue anchor assemblies such that the interface in the gastric lumen is isolated from environmental fluctuations, with each of the second plurality of tissue anchor assemblies including a third tissue anchor engaging a surface of the first fold of tissue, a fourth tissue anchor engaging a surface of the second fold of tissue, and a connector extending through each of the first fold of tissue and the second fold of tissue and looping over both of the first fold of tissue and the second fold of tissue, to connect the third tissue anchor with the fourth tissue anchor.

2. The method of claim 1 further comprising approximating the first fold of tissue and the second fold of tissue into apposition prior to securing, from within the stomach.

3. The method of claim 1 wherein securing, from within the stomach, comprises deploying a first tissue anchor assembly such that the folds of tissue are maintained in apposition relative to one another.

4. The method of claim 3 wherein deploying a first tissue anchor assembly comprises endoscopically deploying the first tissue anchor assembly.

5. The method of claim 3 wherein reinforcing the interface comprises deploying additional tissue anchor assemblies adjacent to the first tissue anchor assembly.

6. The method of claim 3 wherein reinforcing the interface comprises deploying additional tissue anchor assemblies in a staggered pattern relative to the first tissue anchor assembly.

7. The method of claim 1 wherein securing, from within the stomach, comprises endoscopically securing the first fold of tissue to the second fold of tissue from within the stomach.

8. The method of claim 1 wherein securing, from within the stomach, comprises laparoscopically securing the first fold of tissue to the second fold of tissue.

9. The method of claim 1 wherein reinforcing the interface comprises over-sewing the interface with one or more lengths of suture adjacent to the interface.

10. The method of claim 1 wherein reinforcing the interface comprises deploying one or more clips onto the interface between the first and second folds of tissue.

11. The method of claim 1 wherein environmental fluctuations comprise changes in pressure imparted on the interface between the first and second folds of tissue.

12. The method of claim 11 wherein the changes in pressure are imparted by passage of food or fluids through the gastric lumen.

13. The method of claim 11 wherein the changes in pressure are imparted by naturally-occurring contractions throughout the stomach.

14. The method of claim 1 wherein environmental fluctuations comprise naturally-occurring changes in pH levels within the stomach.

15. A method of attenuating environmental fluctuations relative to an approximated region of tissue within a stomach, comprising:

securing, from within the stomach, a first fold of tissue to a second fold of tissue along a first interface between the first and second folds of tissue using a first plurality of tissue anchor assemblies such that a gastric lumen is formed between the first and second folds of tissue, the gastric lumen extending substantially from a gastroesophageal junction of the stomach to at least partially toward a pylorus of the stomach, with each of the first plurality of tissue anchor assemblies including a first tissue anchor engaging a surface of the first fold of tissue inside the gastric lumen, a second tissue anchor engaging a surface of the second fold of tissue inside or outside of the gastric lumen, and a connector extending through each of the first fold of tissue and the second fold of tissue, without looping over either of the first fold of tissue or the second fold of tissue, to connect the first tissue anchor with the second tissue anchor; and securing, from within the stomach, a second plurality of tissue anchor assemblies along a second interface between the first and second folds of tissue in the gastric lumen such that the environmental fluctuations are attenuated relative to a portion of the first or second interface, with each of the second plurality of tissue anchor assemblies including a third tissue anchor engaging a surface of the first fold of tissue, a fourth tissue anchor engaging a surface of the second fold of tissue, and a connector extending through each of the first fold of tissue and the second fold of tissue and looping over both of the first fold of tissue and the second fold of tissue, to connect the third tissue anchor with the fourth tissue anchor.

16. The method of claim 15 further comprising approximating the first fold of tissue and the second fold of tissue into apposition prior to securing, from within the stomach, a first fold of tissue to a second fold of tissue.

17. The method of claim 15 wherein securing, from within the stomach, a first fold of tissue to a second fold of tissue comprises deploying a first tissue anchor assembly such that the folds of tissue are maintained in apposition relative to one another.

18. The method of claim 17 wherein deploying a first tissue anchor assembly comprises endoscopically deploying the first tissue anchor assembly.

19. The method of claim 18 further comprising deploying additional tissue anchor assemblies adjacent to the first tissue anchor assembly.

20. The method of claim 15 wherein the second interface is adjacent to the first interface.

21. The method of claim 20 wherein the second plurality of tissue anchor assemblies forms a staggered pattern relative to the first plurality of tissue anchor assemblies.

22. The method of claim 15 wherein environmental fluctuations comprise changes in pressure imparted on the first interface between the first and second folds of tissue.

23. The method of claim 22 wherein the changes in pressure are imparted by passage of food or fluids through the gastric lumen.

24. The method of claim 22 wherein the changes in pressure are imparted by naturally-occurring contractions throughout the stomach.

25. The method of claim 15 wherein environmental fluctuations comprise naturally-occurring changes in pH levels within the stomach.

* * * * *